(12) United States Patent
Baudenbacher et al.

(10) Patent No.: US 10,082,500 B2
(45) Date of Patent: Sep. 25, 2018

(54) DEVICE AND METHOD FOR DETECTING A TARGET ANALYTE

(71) Applicants: Franz Baudenbacher, Franklin, TN (US); Raymond Mernaugh, Franklin, TN (US); John Mayo, Nashville, TN (US); Brad Lubbers, Madison, TN (US); Robert G. Wiley, Franklin, TN (US)

(72) Inventors: Franz Baudenbacher, Franklin, TN (US); Raymond Mernaugh, Franklin, TN (US); John Mayo, Nashville, TN (US); Brad Lubbers, Madison, TN (US); Robert G. Wiley, Franklin, TN (US)

( * ) Notice: Subject to any disclaimer, the term of this patent is extended or adjusted under 35 U.S.C. 154(b) by 0 days.

(21) Appl. No.: 14/626,885

(22) Filed: Feb. 19, 2015

(65) Prior Publication Data

US 2015/0160205 A1 Jun. 11, 2015

Related U.S. Application Data

(63) Continuation-in-part of application No. 14/466,305, filed on Aug. 22, 2014.
(Continued)

(51) Int. Cl.
*G01N 25/20* (2006.01)
*G01N 33/543* (2006.01)
(Continued)

(52) U.S. Cl.
CPC .. *G01N 33/54306* (2013.01); *B01L 3/502784* (2013.01); *B01L 7/52* (2013.01);
(Continued)

(58) Field of Classification Search
CPC .............. G01N 25/20; G01N 33/54373; B01L 3/502784
(Continued)

(56) References Cited

U.S. PATENT DOCUMENTS 4,151,252 A 4/1979 Marchand et al.
4,822,566 A 4/1989 Newman
(Continued)

FOREIGN PATENT DOCUMENTS

WO 2005017485 A2 2/2005
WO 2015027151 A1 2/2015

OTHER PUBLICATIONS

Torres F E et al., "Enthalpy Arrays," Proceedings of the National Academy of Sciences, National Academy of Sciences, vol. 101, No. 26, Jun. 29, 2004 (Jun. 29, 2004), pp. 9517-9522.
(Continued)

*Primary Examiner* — Brian J. Sines
(74) *Attorney, Agent, or Firm* — Craig A. Phillips; Dickinson Wright PLLC

(57) ABSTRACT

One aspect of the present disclosure relates to a calorimeter for detecting the presence of a target analyte in a fluid sample. The calorimeter can include a support structure, a hermetically-sealed, thermally decoupled central reaction zone associated with the support structure, at least one droplet transport region, and detection electronics. The at least one droplet transport region can be associated with the support structure and configured to merge a reagent droplet with a sample droplet including the fluid sample to form a reaction droplet in the central reaction zone. The detection electronics can be in electrical and/or thermal communication with the central reaction zone and associated with the support structure. The calorimeter can be configured to detect a heat of reaction produced by a reaction event
(Continued)

between the target analyte and a capture reagent upon formation of the reaction droplet.

58 Claims, 14 Drawing Sheets

Related U.S. Application Data

(60) Provisional application No. 61/868,995, filed on Aug. 22, 2013, provisional application No. 61/877,099, filed on Sep. 12, 2013, provisional application No. 61/879,866, filed on Sep. 19, 2013, provisional application No. 61/883,679, filed on Sep. 27, 2013.

(51) Int. Cl.
*B01L 3/00* (2006.01)
*G01N 25/48* (2006.01)
*G01K 17/00* (2006.01)
*B01L 7/00* (2006.01)

(52) U.S. Cl.
CPC ....... *G01K 17/006* (2013.01); *G01N 25/4806* (2013.01); *G01N 33/54373* (2013.01); *B01L 2200/147* (2013.01); *B01L 2300/0636* (2013.01); *B01L 2300/0645* (2013.01); *B01L 2300/0819* (2013.01); *B01L 2300/0867* (2013.01); *B01L 2300/0896* (2013.01); *B01L 2300/1883* (2013.01)

(58) Field of Classification Search
USPC .......... 422/68.1, 50, 51, 82.12, 502; 436/43, 436/518, 501, 147
See application file for complete search history.

(56) References Cited

U.S. PATENT DOCUMENTS

| | | | |
|---|---|---|---|
| 4,888,281 A | 12/1989 | Schochetman et al. | |
| 6,193,413 B1* | 2/2001 | Lieberman ........... | G01K 17/006 374/43 |
| 6,197,494 B1 | 3/2001 | Oberhardt | |
| 6,498,016 B1 | 12/2002 | Nahar et al. | |
| 6,589,746 B1 | 7/2003 | Zemlan | |
| 6,734,425 B2 | 5/2004 | Hantschel et al. | |
| 6,846,654 B1 | 1/2005 | Blackburn et al. | |
| 6,989,130 B2 | 1/2006 | Deshmukh | |
| 7,141,210 B2 | 11/2006 | Bell et al. | |
| 7,147,763 B2 | 12/2006 | Elrod et al. | |
| 7,241,420 B2 | 7/2007 | Hantschel et al. | |
| 7,396,654 B2 | 7/2008 | Hayes et al. | |
| 7,413,706 B2 | 8/2008 | Peeters et al. | |
| 7,416,897 B2 | 8/2008 | Bruce et al. | |
| 7,419,835 B2 | 9/2008 | Torres et al. | |
| 7,435,578 B2 | 10/2008 | Wikswo et al. | |
| 7,473,030 B2 | 1/2009 | Bruce et al. | |
| 7,473,031 B2 | 1/2009 | Wolkin et al. | |
| 7,521,253 B2 | 4/2009 | Bruce et al. | |
| 7,553,669 B2 | 6/2009 | Torres et al. | |
| 7,615,375 B2 | 11/2009 | Torres et al. | |
| 7,632,008 B2 | 12/2009 | Recht et al. | |
| 7,666,680 B2 | 2/2010 | Torres et al. | |
| 7,727,768 B2 | 6/2010 | Bell et al. | |
| 7,745,161 B2 | 6/2010 | Torres et al. | |
| 7,754,492 B2 | 7/2010 | Bell et al. | |
| 7,784,173 B2 | 8/2010 | Wolkin et al. | |
| 7,790,111 B2 | 9/2010 | Torres et al. | |
| 7,816,146 B2 | 10/2010 | Wolkin et al. | |
| 7,833,800 B2 | 11/2010 | Bell et al. | |
| 7,851,226 B2 | 12/2010 | Torres et al. | |
| 7,914,735 B2 | 3/2011 | Torres et al. | |
| 8,075,854 B2 | 12/2011 | Yang et al. | |
| 8,097,421 B2 | 1/2012 | Koo | |
| 8,130,072 B2 | 3/2012 | DeBruyker et al. | |
| 8,173,436 B2 | 5/2012 | Zhang et al. | |
| 8,088,333 B2 | 11/2012 | Ahmad | |
| 8,393,785 B2 | 3/2013 | Iyengar et al. | |
| 8,501,417 B2 | 8/2013 | Pohlmann et al. | |
| 8,617,899 B2 | 12/2013 | DeBruyker et al. | |
| 8,637,138 B2 | 1/2014 | Wolkin et al. | |
| 8,685,216 B2 | 4/2014 | DeBruyker et al. | |
| 8,722,417 B2 | 5/2014 | Ahmad | |
| 8,940,234 B2 | 1/2015 | Zhang et al. | |
| 2002/0169394 A1* | 11/2002 | Eppstein ................. | A61B 5/00 600/573 |
| 2003/0059807 A1* | 3/2003 | Roach .................. | C12Q 1/6825 435/6.11 |
| 2004/0007740 A1 | 1/2004 | Abstreiter et al. | |
| 2004/0038426 A1* | 2/2004 | Manalis ........... | C01N 33/54366 436/514 |
| 2006/0264780 A1* | 11/2006 | Holmes ................ | A61B 5/1411 600/583 |
| 2008/0004542 A1* | 1/2008 | Allen ..................... | A61B 5/411 600/532 |
| 2009/0226890 A1* | 9/2009 | Haik ................. | G01N 33/56911 435/5 |
| 2010/0024572 A1* | 2/2010 | Roukes ................... | G01L 1/044 73/862.625 |
| 2012/0267693 A1 | 10/2012 | Holm-Kennedy | |
| 2014/0092935 A1* | 4/2014 | Lin ........................ | G01N 25/48 374/10 |
| 2015/0079583 A1 | 3/2015 | Baudenbacher et al. | |
| 2015/0160205 A1 | 6/2015 | Baudenbacher et al. | |
| 2015/0177233 A1* | 6/2015 | Puntambekar ........ | B01L 3/5027 436/501 |

OTHER PUBLICATIONS

Mukherjee T, "Design Automation Issues for Biofluidic Microchips," Computer-aided design, 2005. ICCAD-2005, IEEE/ACM International Conference on Nov. 6-10, 2005, Piscataway, NJ, USA, pp. 463-470.

Zhang et al., Calorimetric biosensors with integrated microfluidic channels, Biosensors and Bioelectronics 19 (2004), pp. 1733-1743.

Wang et al., A MEMS Thermal Biosensor for Metabolic Monitoring Applications, Journal of Microelectromechanical Systems, vol. 17, No. 2, Apr. 2008, IEEE.

Lerchner et al., Nano-calorimetry of small-sized biological samples, Thermochimica Acta 477 (2008), pp. 48-53, Aug. 28, 2008.

Xu et al., A Microfabiracated Nanocalorimeter: Design, Characterization, and Chemical Calibration, Analytical Chemistry, vol. 80, No. 8, Apr. 15, 2008, pp. 2728-2733.

Johannessen et al., A Suspended Membrane Nanocalorimeter for Ultralow Volume Bioanalysis, IEEE Transactions on Nanobioscience, vol. 1, No. 1, Mar. 2002, pp. 29-36.

\* cited by examiner

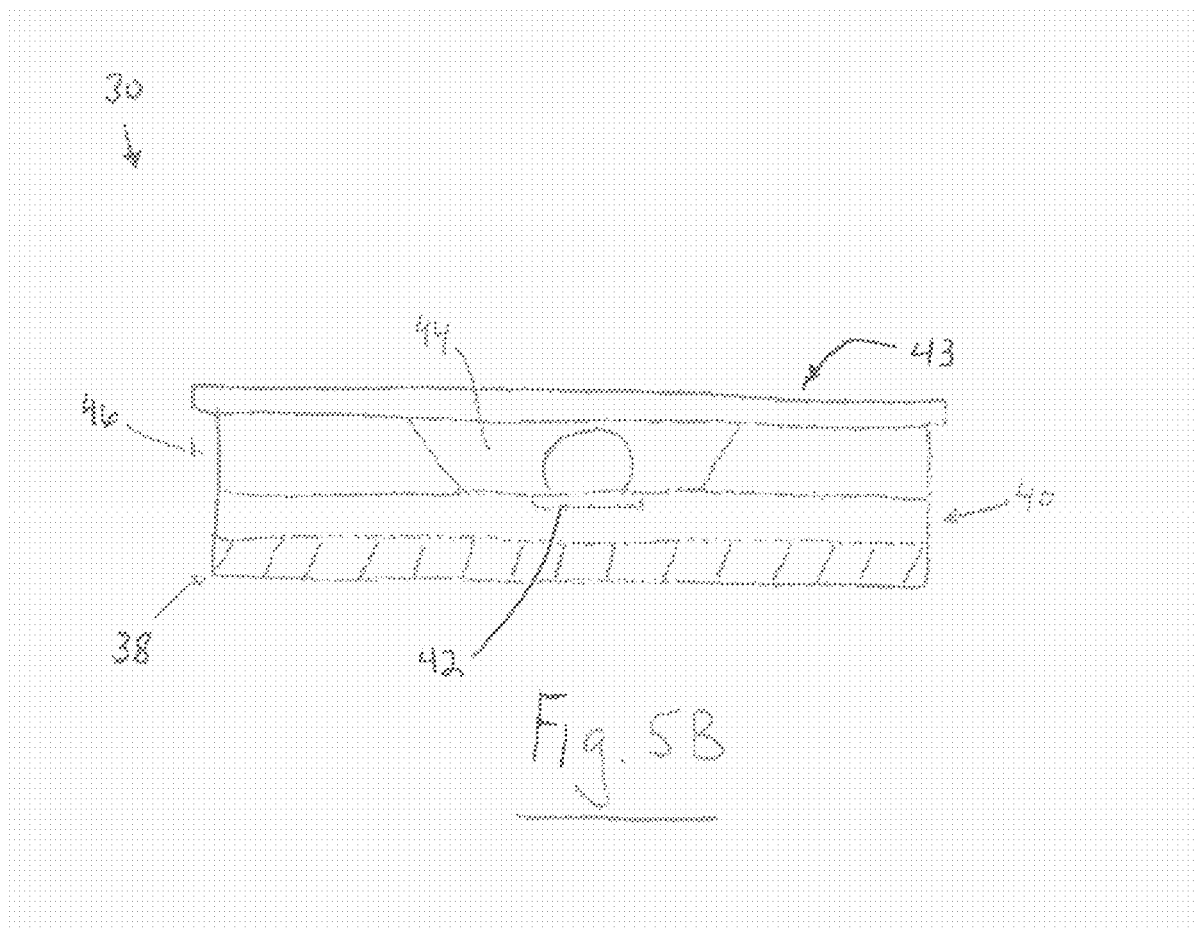

DEVICE AND METHOD FOR DETECTING A TARGET ANALYTE

RELATED APPLICATIONS

This application claims the benefit as a continuation-in-part application of U.S. application Ser. No. 14/466,305, filed on Aug. 22, 2014, which claims the benefit of U.S. Provisional Patent Application Ser. Nos. 61/868,995, filed Aug. 22, 2013, 61/877,099, filed on Sep. 12, 2013, 61/879,866, filed Sep. 19, 2013, and 61/883,679, filed Sep. 27, 2013. Each of the aforementioned applications is hereby incorporated by reference in its entirety for all purposes.

STATEMENT REGARDING FEDERALLY SPONSORED RESEARCH

None.

TECHNICAL FIELD

The present disclosure relates generally to diagnostic devices and methods for rapid, inexpensive, highly sensitive and specific detection of target analytes using nanocalorimetry with a functionalized surface to capture analytes in combination with an enzyme amplification strategy for use in a variety of settings and industries, such as healthcare, agriculture, food industry, veterinary, drug discovery, defense and homeland security.

BACKGROUND OF THE INVENTION

Currently there is no completely integrated, affordable, point-of-care (POC) or point-of-need diagnostic platform that is rugged, durable, and that provides results in minutes with a high level of sensitivity and specificity that may be operated with little training. This problem applies to diagnosing/detecting bacteria, viruses, fungi, pathogens, biomarkers and industrial processes, as well as chemical and biological warfare agents. Existing diagnostic platforms are very expensive in terms of both the equipment and the actual test performed, require a laboratory or hospital setting, require highly trained technicians, require expensive infrastructure, and take from hours to days to obtain results. This current time to deliver results and the current cost of getting these results ultimately means lost lives, health, and money when utilizing current technologies.

Recent development with existing detection technologies of biological binding events and cellular activity have improved over time to the point where they are now limited by the first principles of the binding affinity of the targets or targeted pairs (e.g., antibody-antigen, etc.), or the amount of cellular activity when measuring metabolic activity. The weaker binding events and lower cellular metabolic rates are below the noise floor of these technologies, however, thereby rendering it hard to impossible to detect such events as those limits are reached. Therefore, it is critical to integrate robust enzyme amplification strategies with micro-machined calorimeters with a small thermal mass and fast response times into future assay technologies.

SUMMARY OF THE INVENTION

One aspect of the present disclosure relates to a calorimeter and signal amplification method for detecting the presence of a target analyte in a fluid sample. The calorimeter can include a support structure; a hermetically-sealed; thermally decoupled central reaction zone associated with the support structure, a temperature sensor, at least one droplet transport region and reagent reservoirs, and detection electronics. The at least one droplet transport region can be associated with the support structure or another support structure forming a lid to seal the device and configured to merge a reagent droplet with a sample droplet including the fluid sample to form a reaction droplet in the central reaction zone. The detection electronics can be in electrical and/or thermal communication with the central reaction zone and associated with the support structure. The calorimeter can be configured to detect the heat of reaction produced by a reaction event between the target analyte and a capture/detection reagent or an enzyme amplification step where an enzyme labels the target analyte and turns over the enzyme's substrate to produce a larger thermal signature.

In one design implementation of the calorimeter device the thermal central reaction zone is part of a thin membrane which has a low thermal conductivity which allows for thermal insulation relative to the support structure at room temperature. Thin film tracks of two dissimilar metals are deposited directly onto the thin membrane and form a thermopile. As known to one of skill in the art, a thermopile is an electrical device that converts thermal energy into electrical energy and it is composed of a plurality of thermocouples, usually arranged in series, although they can be arranged in parallel, designed to respond to changes in thermal energy in a system. The dissimilar metals forming the thermocouple are selected to achieve a high Seebeck coefficient. The hot junctions of the thermopile are directly in the central reaction zone while the cold junctions are outside of the central reaction zone. Reducing the thickness or thermal conductivity of the membrane, placing the thermopiles directly into the reaction zone and reducing the size of the membrane to host nanoliters of sample volumes increases the thermal energy sensitivity to <1 nanoJoules, reduces mixing times and the time constant tau of the device. Tau is given by the ratio of total thermal mass $C_{tot}$ to the total thermal conductivity $G_{tot}$ and should be less than 1 second. The energy sensitivity is given by the total Seebeck coefficient and the total thermal conductance. The total thermal conductivity encompasses all the heat fluxes away from the sample through the membrane, thermopiles and radiation. It should be noted that increasing sample volume increases $G_{tot}$ and therefore decreases the energy sensitivity.

Another aspect of the disclosure relates to a method to increase the sensitivity of the device and amplification of the thermal signal due to the presence of an analyte in the sample volume. In order to amplify the heat generated by the reaction, the thermally isolated central reaction zone includes a functionalized surface for the capture of the analyte and an enzyme amplification step. Passing multiple sample droplets over the functionalized surface can increase the amount of analyte captured on the surface. Because we are using nanoliter sized droplets the surface to volume ratios are large and the diffusion times small therefore decreasing the assay time. Second, in an enzyme amplification step a secondary capture agent linked with an enzyme, a labeling enzyme, is used to bind to the analyte captured by the functionalized surface and then reagent for the enzyme is added and the thermal signature from the enzymatic reaction is detected by the nanocalorimeter. Since we can introduce high concentrations of enzymatic substrate and each enzyme molecule turns over multiple substrate molecules the sensitivity of the device is greatly enhanced. The sensitivity is improved through this amplification step, which generates a large thermal signature, which decays over time as all the enzyme substrate is turned over. The time course and the size of the signal can be predicted using a mathematical model including only parameters characterizing the physical properties of the device and the activity of the enzyme. Therefore, we can determine the amount of enzyme bound by the analyte and therefore the absolute analyte concentration.

In another implementation of the method the thermal signal can be further amplified by exposing the labeling enzyme to multiple droplets with a fixed amount of enzyme substrate. The labeling enzyme is bound to the analyte which is immobilized on the calorimeter surface. The exothermic reaction of the enzyme converting its substrate can be repeated multiple times by bringing in discrete amounts of substrate and using box car and signal averaging techniques to increase the signal to noise ratio. It should be noted that this method of signal amplification does not require the use of any more sample and is therefore ideally suited for applications where multiple analytes are detected simultaneously. Depending on the reaction catalyzed by the enzyme the substrate can be a chemical, small molecule, a biological sample, a DNA or RNA fragment or any other enzyme specific substrate. The present invention allows for selecting an enzyme tailored to the analyte levels expected. Thus, for some detection processes for certain analytes one needs an enzyme with a higher turnover rate and a higher heat of reaction than for other analytes.

Another aspect of the present disclosure relates to a method for detecting a target analyte in a fluid sample. The method can entail the use of a calorimeter that includes a support structure, a hermetically-sealed and thermally decoupled central reaction zone associated with the substrate, at least one sample droplet transport region and reagent reservoirs associated with the support structure and configured to merge one or more reagent droplets with a sample droplet comprising the fluid sample, and detection electronics in electrical and/or thermal communication with the central reaction zone and associated with the substrate. One step of the method can include depositing a sample droplet within the central reaction zone, preferably through use of the sample droplet transport region. Next, a reagent droplet can be merged with the sample droplet in the central reaction zone to form a reaction droplet. The calorimeter can then detect an electronic signal generated upon formation of the reaction droplet. The electronic signal can be indicative of the heat of reaction produced by a reaction event, such as a binding event, between the target analyte in the sample droplet and a capture/detection reagent in the reagent droplet.

Another aspect of the present disclosure relates to a method for detecting a target analyte in a fluid sample in a point-of-care environment. The method can entail the use of a calorimeter as described above, a hermetically-sealed, thermally decoupled central reaction zone associated with the substrate, the central reaction zone including a temperature sensor and a surface at least partially coated with a capture reagent that specifically binds the target analyte, a first droplet transport region associated with the substrate, a second droplet transport region associated with the substrate, a third droplet transport region associated with the substrate, and detection electronics in electrical and/or thermal communication with the central reaction zone and associated with the substrate. The central reaction zone is functionalized with a capture surface to immobilize the analyte onto the calorimeter. One step of the method can include depositing a nanoliter-sized sample droplet within the central reaction zone having the functionalized capture surface. Next the sample droplet is washed away with a buffer solution to remove unbound analyte and the rest of the sample. Next, a first droplet comprising a labeling agent coupled with a reactive moiety, like an enzyme, can be guided along the first droplet transport region until the droplet covers the reaction zone. The labeling agent binds to the analyte that is already captured by the functionalized surface. Now the unbound labeling agent is washed away and a droplet comprising a reaction substrate for the enzyme brought in by the labeling agent can then be guided along the second droplet transport region until the droplet is placed on the reaction zone. The calorimeter can then detect an electronic signal generated upon turnover of substrate by the enzyme bound to the labeling compound. The electronic signal can be indicative of the heat of reaction produced by a reaction between the reactive moiety, enzyme, and the enzyme reaction substrate that occurs when the target analyte is present in the fluid sample.

In one embodiment the present invention is a method of detecting a target analyte in a fluid sample, using an analysis device including a supporting structure configured to receive an insert having a calorimeter and a surface which is capable of being functionalized with a specified bound analyte: binding a sample to the specified bound analyte; applying a secondary capture agent including an enzyme to the functionalized surface; allowing the secondary capture agent to bind to the specified bound analyte; removing any unbound secondary capture agent from the functionalized surface; applying a substrate configured to react with at least one of the secondary capture agent and the sample generating a thermal change; measuring a generated thermal change over a specified time period.

In another embodiment the present invention is a method of detecting a target analyte in a fluid sample, using an analysis device including a supporting structure configured to receive an insert having a calorimeter and a surface which is capable of being functionalized with a specified bound analyte: measuring a sample volume of less than 100 nL; binding a sample to the specified bound analyte; applying a secondary capture agent including an enzyme to the functionalized surface; allowing the secondary capture agent to bind to the sample; removing any unbound secondary capture agent from the functionalized surface; applying a substrate configured to react with at least one of the secondary capture agent and the sample generating a thermal change; measuring the generated thermal change over a specified time period.

In another embodiment the present invention is a method of detecting a target analyte in a fluid sample, using an analysis device comprising the steps of: providing an insert having a calorimeter and a surface which is functionalized with a specified bound analyte: receiving a sample; measuring a sample volume of less than 100 nL; applying the measured sample volume, from said step of measuring, to the specified bound analyte; measuring the generated thermal change over a specified time period from a reaction between the target analyte in the sample and the specified bound analyte; and determining the presence or absence of the target analyte in the sample.

In another embodiment the present invention is a method of detecting a target analyte in a fluid sample, using an analysis device including a supporting structure configured to receive an insert having a calorimeter and a surface having a reaction zone and a control zone: applying the sample to at least the reaction zone; applying a substrate to the reaction zone and the control zone; measuring the generated thermal difference over a specified time period between the reaction zone and the control zone; continue applying the substrate to the reaction zone and the control zone during said step of measuring the generated thermal difference until the temperature difference between the reaction zone and the control zone is less than a specified differential; and generating an output related to the presence or absence of the target analyte in the sample.

In another embodiment the present invention is a method of detecting a target analyte in a fluid sample, using an analysis device including a supporting structure configured to receive an insert having a calorimeter and a surface having a reaction zone and a control zone; applying the sample to at least the reaction zone; measuring the generated thermal difference over a specified time period between the reaction zone and the control zone; and generating an output related to the presence or absence of the target analyte in the sample.

In another embodiment the present invention is a device for detecting a target analyte comprising: a supporting structure; a sample measuring apparatus supported by the supporting structure and including: a surface including a thermally conductive layer having reaction zone and a control zone; a thermopile operationally coupled to said reaction zone and said control zone on said thermally conductive layer; and a thermally insulated layer configured to insulate at least the reaction zone.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 5B is a cross-sectional view taken along Line 5B-5B in FIG. 5A;

DETAILED DESCRIPTION OF A PREFERRED EMBODIMENT

Definitions

Figure 1:
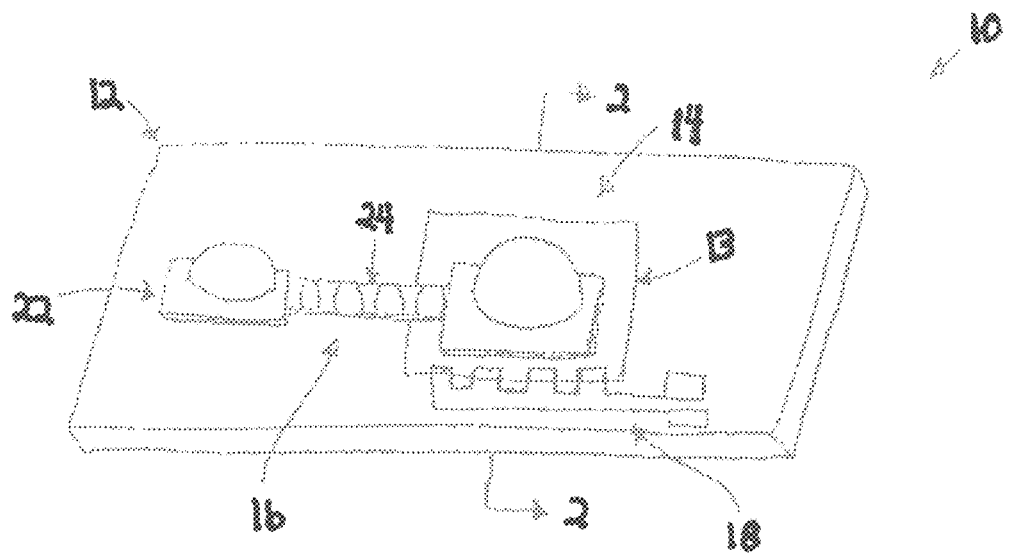
FIG. 1 is schematic illustration showing a calorimeter for detecting the presence of a target analyte in a fluid sample constructed in accordance with one aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature may not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the terms "about" or "approximately" can generally mean within 20 percent, preferably within 10 percent, and more preferably within 5 percent of a given value or range. Numerical quantities given herein are approximate, meaning that the term "about" or "approximately" can be inferred if not expressly stated.

As used herein, the term "subject" can refer to any warm-blooded organism including, but not limited to, human beings, pigs, rats, mice, dogs, goats, sheep, horses, monkeys, apes, rabbits, cattle, etc.

As used herein, the term "target analyte" or "analyte" refers to a substance in a fluid sample capable of being detected and analyzed by the present disclosure. Target analytes can include, but are not limited to, molecules, peptides, proteins (including prions) and fragments thereof, nucleic acids, oligonucleotides, cells, microorganisms (e.g., viruses, bacteria, and fungi) and fragments and products thereof, enzyme substrates, ligands, carbohydrates, hormones, sugar, metabolic byproducts, cofactors, pollutants, chemical agents, small molecules, drugs, toxins, plants and fragments and products thereof, biomarkers indicative of a disease or disorder, and any substance for which attachment sites, binding members or receptors can be developed.

As used herein, the term "fluid sample" can refer to any quantity of a liquid or fluid that comprises one or more target analytes and that can be used with the present disclosure. For example, a fluid sample can be extracted from a biological sample derived from humans, animals, plants, fungi, yeast, bacteria, viruses, tissue cultures or viral cultures, or a combination of the above. In some instances, a fluid sample can comprise a bodily fluid, such as serum, blood, urine, sputum, seminal or lymph fluids. A fluid sample can also be an environmental sample, such as samples obtained from rivers or soil. A fluid sample can be first purified or partially purified, for example, and/or mixed with buffers and/or reagents that are used to generate appropriate conditions for successfully performing a method of the present disclosure.

As used herein, the term "electrical communication" can refer to the ability of a generated electric field to be transferred to, or have an effect on, one or more components of the present disclosure. In some instances, the generated electric field can be directly transferred to a component (e.g., via a wire or lead). In other instances, the generated electric field can be wirelessly transferred to a component.

As used herein, the term "thermal communication" can refer to an efficient thermal conductivity between two or more components of the present disclosure, which may or may not be in direct contact with one another (e.g., there may be one or more intervening components, structures, or elements between first and second components in thermal communication with one another). In some instances, "thermal communication" can be conductive, convective, radiative, or any combination thereof.

As used herein, the term "capture reagent" or "labeling agent" can refer to any agent that is capable of binding to, or reacting with, a target analyte. In some instances, a "capture reagent" can include an agent that is capable of specifically binding to a target analyte, i.e., having a higher binding affinity and/or specificity to the target analyte than to any other moiety. Any agent can be used as a capture reagent so long that it has the desired binding affinity and/or specificity to the target analyte. Examples of capture reagents can include, but are not limited to, antibodies, antibody fragments, recombinant antibodies and fragments thereof, native, synthetic, or recombinant peptides or proteins, peptoids, cell receptors and fragments thereof, enzymes, enzymes involved in the production of reactive oxygen species or breakdown, enzymes that catalyze a reaction leading to a product that may be of research, diagnostic or therapeutic use, p450 enzymes, glycoproteins, oligonucleotides, nucleic acids (e.g., RNA, DNA, RNA/DNA hybrids), peptide-nucleic acids, vitamins, sugars, oligosaccharides, carbohydrates, lipids, lipoproteins, small molecules, chemical compounds (e.g., hydrogen peroxide), cells, a cellular organelle, an inorganic molecule, an organic molecule, and mixtures or complexes thereof. It will be appreciated that capture reagents may also be coupled to certain substrates, such as microbeads or to enzymes.

As used herein, the term "heat of reaction" can refer to the heat evolved or absorbed during a chemical and/or physical reaction taking place under conditions of constant temperature and of either constant volume or constant pressure.

As used herein, the term "reaction event" can refer to any one or combination of molecular interactions between a target analyte and a capture reagent that generates or produces a heat of reaction.

As used herein, the term "in fluid communication" can refer to a fluid (e.g., a liquid) that can move from one part of the present calorimeter to another part of the calorimeter. The two or more parts of the calorimeter can be in fluid communication by being physically linked together or adjacent to each other, or the fluid communication can be mediated through another part of the calorimeter.

As used herein, the term "microcalorimeter" can refer to a calorimeter capable of detecting very small enthalpic changes (e.g., in the range of microcalories) using microliter-sized assay volumes.

As used herein, the term "nanocalorimeter" can refer to a calorimeter capable of detecting very small enthalpic changes (e.g., in the range of nanocalories, 1 nanocalorie is equal to 4.184 nanoJoules) using nanoliter-sized assay volumes.

As used herein, the term "point-of-care environment" can refer to real-time diagnostic testing that can be done in a rapid time frame so that the resulting test is performed faster than comparable tests that do not employ the present disclosure. For example, an ELISA according to the present disclosure can be performed in less time than a conventional ELISA (i.e., less than about 30 minutes, preferably less than 15 minutes, and more preferably less than 10 minutes). Point-of-care environments can include, but are not limited to: emergency rooms; at a bedside; in a stat laboratory; operating rooms; hospital laboratories and other clinical laboratories; doctor's offices; in the field; or in any situation or locale where a rapid and accurate result is desired. In some instances, a subject from which a fluid sample is being assayed can be present, but such presence is not required.

As used herein, the term "reaction substrate" can refer to any substance upon which a reactive moiety can act (e.g., bind or enzymatically convert) to produce or generate a heat of reaction. In one example, a reaction substrate can include an enzymatic substrate, such as hydrogen peroxide, phosphate esters, p-nitrophenyl phosphate (PNPP), 2,2'-Azinobis[3-ethylbenzothiazoline-6-sulfonic acid]-diammonium salt (ABTS), o-phenylenediamine dihydrochloride (OPD), 3,3',5,5'-tetramethylbenzidine (TMB), 3,3' diaminobenzidine (DAB), urea, and beta-galactosides (e.g., 4-methylumbelliferone b-D-galactopyranoside).

As used herein, the term "labeling agent" can refer to a compound or other agent used to label a molecule or molecules of interest, such as a capture reagent, a target analyte, and/or a reactive moiety, thereby providing a detectable signal for subsequent detection. In some instances, a labeling agent can include a compound or agent (e.g., an antibody) that specifically binds to a target analyte and includes a detectable moiety coupled thereto. The labeling agent need not itself carry a detectable moiety, but may instead be a component that is subsequently used to bind a detectable label. For example, the labeling agent can include a first specific binding partner, such as biotin, and a second specific binding partner, such as avidin or streptavidin that carries a detectable moiety.

As used herein, the term "reactive moiety" can include any agent, molecule, or compound capable of reacting with a reaction substrate to produce or generate a heat of reaction. In some instances, a reactive moiety can be coupled to a labeling agent. In one example, a reactive moiety can be an enzyme including, but not limited to, horseradish peroxidase, catalase, alkaline phosphatase, urease or beta-galactosidase.

The present disclosure relates generally to diagnostic devices and methods for rapid, inexpensive, and highly sensitive and specific detection of target analytes in a variety settings and industries, such as healthcare, agriculture, industry, veterinary, drug discovery, defense and homeland security. Essential to all chemical reactions, molecular interactions, and biological processes, is the transfer of energy according to the laws of thermodynamics. This energy flow must result in a change in energy and can be measured according to the first law of thermodynamics:

$$\Delta U = Q - W$$

wherein $\Delta U$ is the change in internal energy, $Q$ is the heat added or taken out of the system, and $W$ is the work performed by or on the system. This formulation of the first law of thermodynamics uses the sign convention of Clausius as opposed to the IUPAC system. Using the IUPAC system the formulation is: $\Delta U = Q + W$ wherein $\Delta U$ is the change in internal energy in the closed system, $Q$ is the heat and $W$ is the work and wherein all net energy transfers to the system are considered positive and all net energy transfers from the system are considered negative. In a closed system, U must remain constant, so all processes that produce work either consume or produce heat, and this heat can be measured.

The field of isothermal calorimetry deals with measuring this heat and characterizing reactions and processes based on it. The more accurately and quickly that temperature changes can be measured, the more details about the process that can be elucidated. In the interest of maximizing calorimeter performance, there is a drive towards smaller sample volumes. This maximizes sensitivity $P = S_{tot}/G_{tot}$ which is the ratio between total Seebeck Coefficient ($S_{tot}$) and total thermal conductivity ($G_{tot}$) and minimizes the time constant $\tau = C_{tot}/G_{tot}$ by reducing the total thermal mass $C_{tot}$ of the sample/device at a fixed total thermal conductivity $G_{tot}$. The total thermal conductivity $G_{tot}$ between the reaction volume and the device support structure needs to be reduced in order to maximize sensitivity. In the present invention is has been unexpectedly found that small sample volumes provide various advantages to use of the present invention. Normally, in ELISA methods larger sample volumes are required to enhance detection of low levels of analytes. Such large sample volumes are, in the present invention, not desirable. Smaller sample volumes in the present invention reduce the total thermal conductivity $G_{tot}$ which is composed of membrane, thermopiles, air and sample volume. Larger sample volumes lead to greater thermal shortening of the membrane decreasing device performance, this is an unexpected result. This makes use of the nanocalorimeters unique in that the use of very small sample sizes is an advantage as opposed to a typical ELISA assay wherein large samples sizes are advantageous. Calorimeter sensitivity can be further improved by reducing $G_{tot}$ through the use of vacuum insulation, thermopile materials with low thermal conductivity and low thermal conductivity membrane materials like photo-definable Su-8 or other polymers like Parylene, or Polyimides like Kapton from DuPont. Su-8 is the trade name for a series of epoxy-based polymers that are negative photoresist polymers used in fabrication of microfluidic devices. Similarly, Parylene is the trade name for a series of poly(p-xylylene) polymers that are photoresists. These photoresist polymers are used to form patterned coatings on surfaces and thereby form microfluidic devices and nanocalorimeters like the present invention. The thermal conductivity of the thermopile material can also be reduced by decreasing the thickness of the material and the width of the material. The intrinsic noise of the nanocalorimeter is given by the Johnson noise of the thermopile and therefore the total resistance of the thermopile. In order to optimize the intrinsic noise performance one has to select materials with a high Seebeck coefficient and low resistance. The Seebeck coefficient, which is also known as thermopower, thermoelectric power, or thermoelectric sensitivity of a material, is a measure of the magnitude of an induced thermoelectric voltage in response to a temperature difference across that material, as induced by the Seebeck effect. Therefore, a given material system for the thermopiles has to be optimized for low electrical resistance and thermal conductivity. Our disclosed design can be built with conventional microfabrication methods such as, photolithography and thin film deposition techniques with micron resolutions in a batch process.

In one embodiment the present invention comprises the following. A nanocalorimeter system with a sensitive thermopile is used to measure very small changes in thermal levels caused by the presence of a target analyte. In this embodiment, the photoresistive polymers are used to create the thermopile and thermocouples formed from two dissimilar metals. The photoresistive polymers are used to create the microfluidics channels and structures as known to those of skill in the art. The design can also include various microfluidics components to move, split and merge drops of samples and reagents. In the basic design the central reaction zone is thermally isolated from the rest of the device and includes a nanocalorimetry thermopile in it. At least a portion of the central reaction zone is functionalized with a capture reagent. Often the capture reagent is an antibody to the target analyte, however it can be any component that binds to the target analyte. The functionalization can also include pre-coating the central reaction zone with gold nanoparticles to enhance binding of the capture reagent to the surface. In use of the device, a fluid suspected of containing the target analyte is then exposed to the functionalized surface and any heat of reaction is detected by the thermopile as an electrical change. This heat of reaction can be caused by binding of the target analyte to the capture reagent.

For some binding events between a capture reagent and a target analyte the heat of reaction is too low to be measured relative to the background noise even with repeated exposures and utilization of box car signal averaging and other known electrical signal enhancement techniques. For these reactions the basic method includes additional steps. In this embodiment, enzyme linked secondary capture reagents are utilized. The basic method is as above with the following steps. After binding of the target analyte to the functionalized surface unbound analyte is washed off. Then a second capture reagent have an enzyme conjugated or linked to it is exposed to the target analyte bound to the functionalized surface. This binding can also generate a binding thermal signature that might be detectable. Then unbound second capture reagent is preferably washed out of the central reaction zone. At this point, the complex is functionalized surface with capture reagent bound to the target analyte and secondary capture reagent, which has a conjugated enzyme linked to it, also bound to the analyte. Then one adds the enzyme substrate and measures the heat signature produced by the enzymatic reaction. In this way the thermal signature is highly enhanced since the thermal signature is limited only by available substrate for the enzyme and the actual heat of the reaction. This greatly enhances the thermal signature. For certain target analytes, the present invention can be used to quantify the amount of target analyte in a sample; for other target analytes detecting the presence or absence of the target analyte without quantification is sufficient. Thus, the amount of heat signature does not necessarily have to be quantitative for certain target analytes.

As described in more detail below, the present disclosure advantageously provides a calorimeter design capable of sub-nanowatt sensitivity based on reducing the thermal mass and total conductance of the calorimeter. Reducing the tau time constant of the ratio between the total thermal mass $C_{tot}$ and total thermal conductivity $G_{tot}$ to below 1 second increases our ability to detect heat generated by reactions taking place in the reaction volume. Therefore, the reaction volume is kept small in the central reaction zone part of the thermally isolated low thermal conductivity membrane. Since the sensitivity is inversely proportional to the total thermal conductance this quantity has to be minimized to improve device performance. A thin film thermopile structure with hot junctions in the reaction volume and cold junctions on the support structure are used in one implementation to measure small temperature changes induced in the reaction volume by reaction between the target analyte and the capture reagent(s). $G_{tot}$ is compromised of the thermal conductance of the membrane, the sample droplet, the thermopile and air surrounding the device.

In one implementation of the device the central reaction zone is comprised of a thin surface which is functionalized/coated with a capture reagent which reacts with the analyte in the sample to generate heat indicative of the concentration of the analyte in the sample. The reagent can be precoated onto the calorimeter surface. Therefore the detection step only requires addition of the sample droplet, which makes it ideally suited for POC applications. The sample droplet needs to be delivered to the central reaction zone while maintaining thermal insulation. A merging of droplets is not required. This is possible through capillary action or digital microfluidics as known to those of skill in the art.

The integration of digital microfluidics with the calorimeter design described allows for repeatable and efficient fluid sample delivery for more complex assays. An enzyme amplification step or substrate driven signal averaging can easily be added to the process to increase the sensitivity to detect a target analyte as described in more detail below. Digital microfluidics provides only one method for an efficient fluid sample handling system while not adversely affecting calorimeter sensitivity providing thermal insulation and low thermal mass.

Advantageously, the combination of nanoscale calorimetry with digital microfluidics provides a scalable multiplexable measurement system applicable to a number of disciplines and fields, such as isothermal titration calorimetry for drug interaction screening, cellular metabolism, biomarker detection, direct measurement of extracellular ATP levels, and new types of calorimetric bioassays.

One Nanocalorimeter Design

Figure 2:
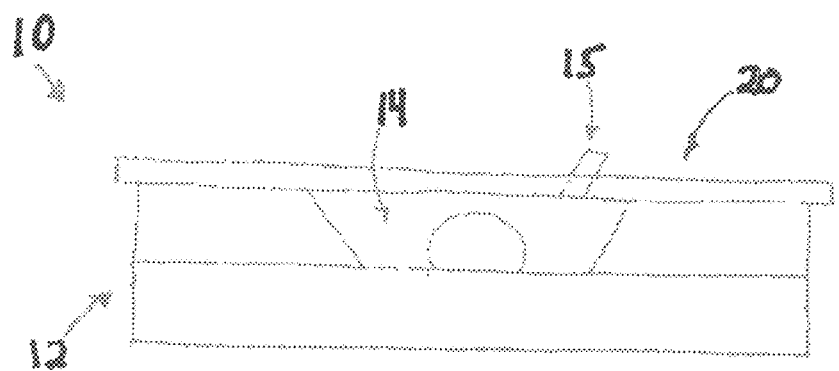
FIG. 2 is a cross-sectional view taken along Line 2-2 in FIG. 1.

One aspect of the present disclosure can include a nanocalorimeter 10, FIGS. 1 and 2, for detecting the presence of a target analyte in a fluid sample. The calorimeter 10 can comprise a support structure 12, a thermally decoupled central reaction zone 14 associated with the support structure 12 and thermal sensors 18, such as a thermopile, in electrical and/or thermal communication with the central reaction zone 14 and associated with the support structure 12. The design of the device 10 is as such that the time constant tau given by the ratio of total thermal mass $C_{tot}$ of the device to the total thermal conductivity $G_{tot}$ by which the reaction zone is thermally linked to the support structure 12 is on the order of less than 1 second.

In one implementation the reaction volume is hermetically-sealed to prevent evaporation and reduce environmental interference.

In another implementation at least one droplet transport region 16 is associated with the support structure 12 and configured to merge a reagent droplet with a sample droplet comprising the fluid sample to form a reaction droplet in the central reaction zone 14. The calorimeter 10 can be configured to detect a heat of reaction produced by a direct reaction event between the target analyte and a capture reagent upon formation of the reaction droplet or the exposure of the capture reagent coated calorimeter surface with the sample droplet. In this implementation no digital microfluidics is required.

Figure 12:
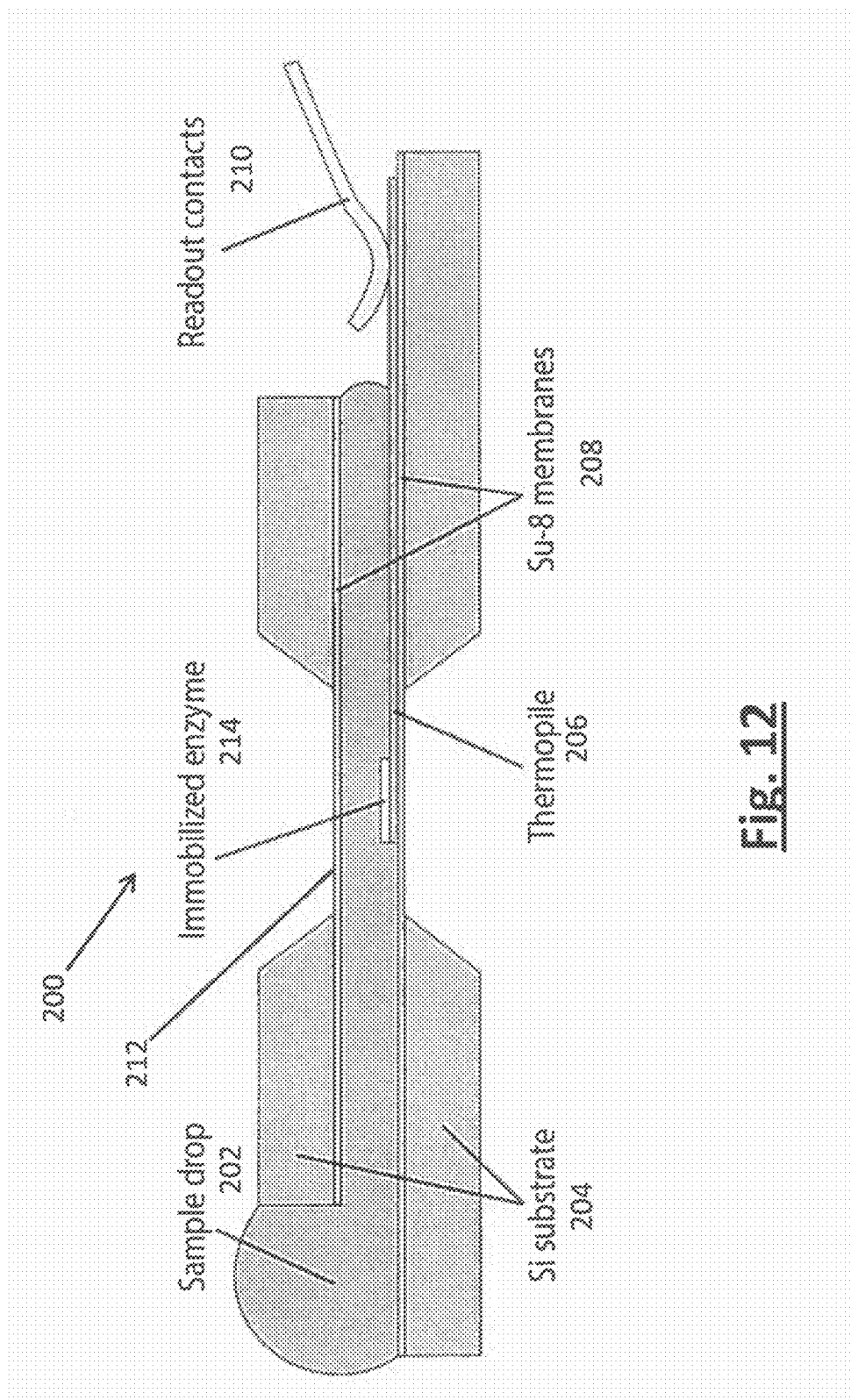
FIG. 12 is a schematic of another embodiment of the present invention utilizing a capillary system to deliver fluid to the calorimeter.
Figure 13:
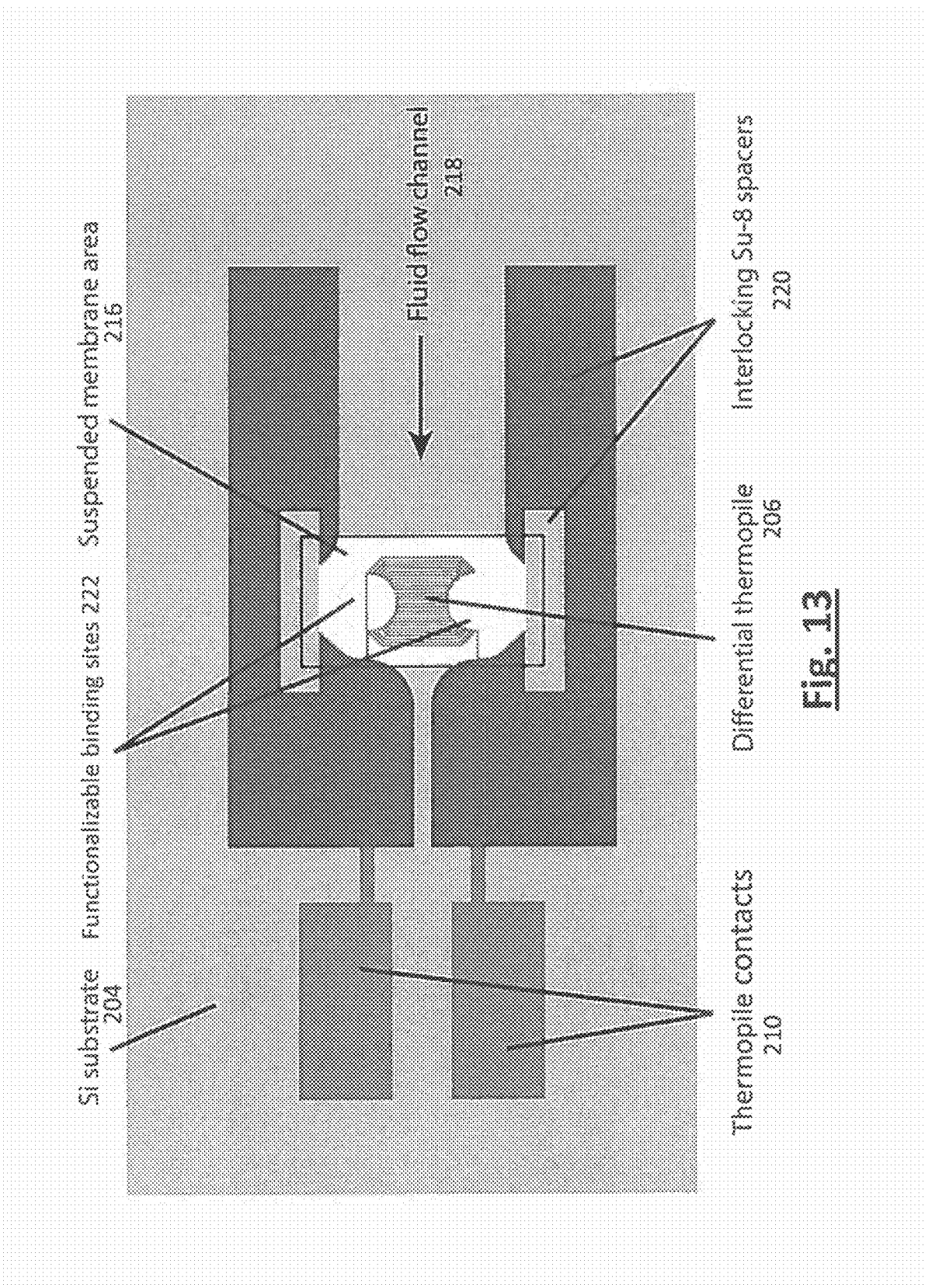
FIG. 13 is another view of a portion of the embodiment shown in FIG. 12.
Figure 14:
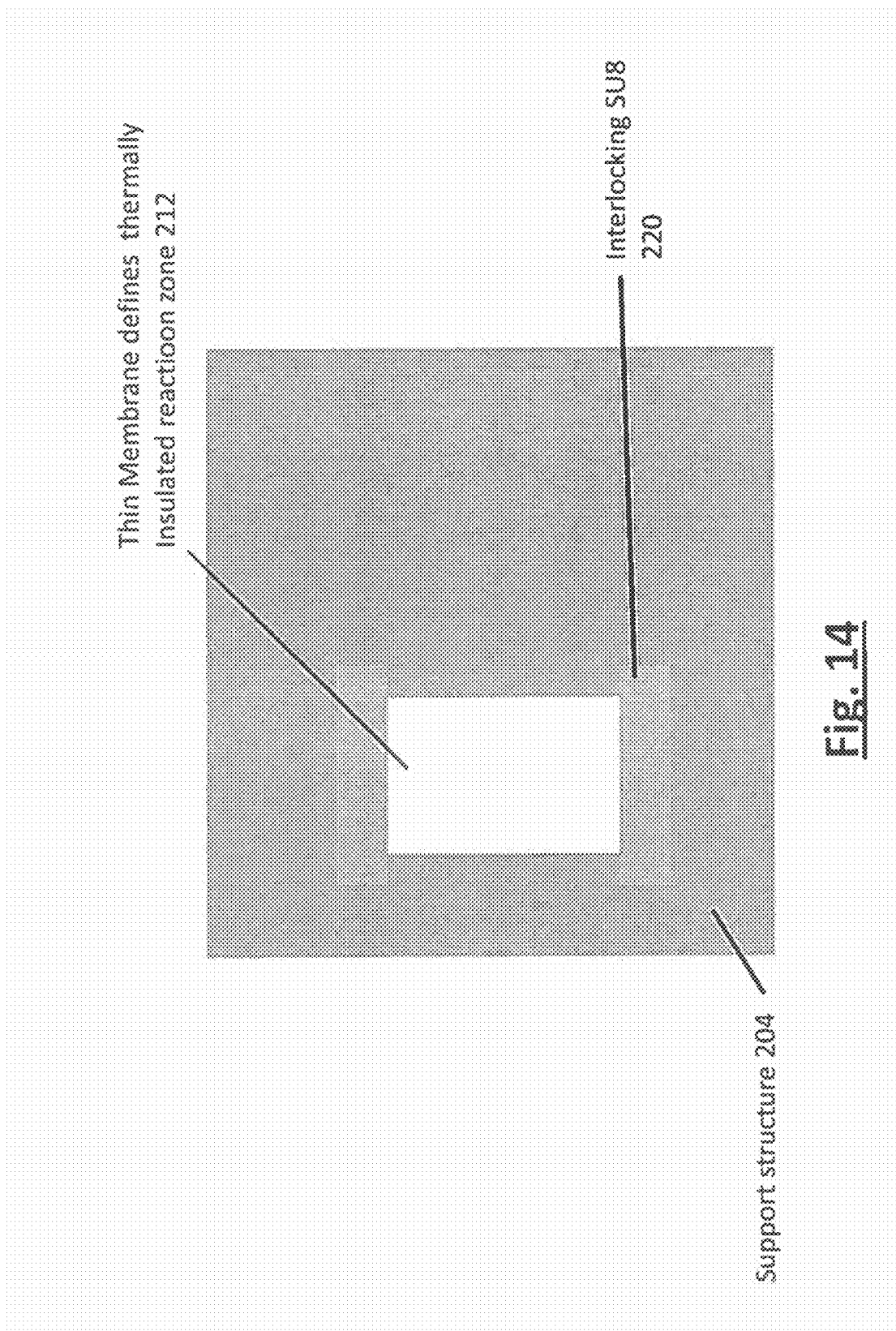
FIG. 14 is a view of the top support structure of the embodiment shown in FIG. 12.
Figure 15:
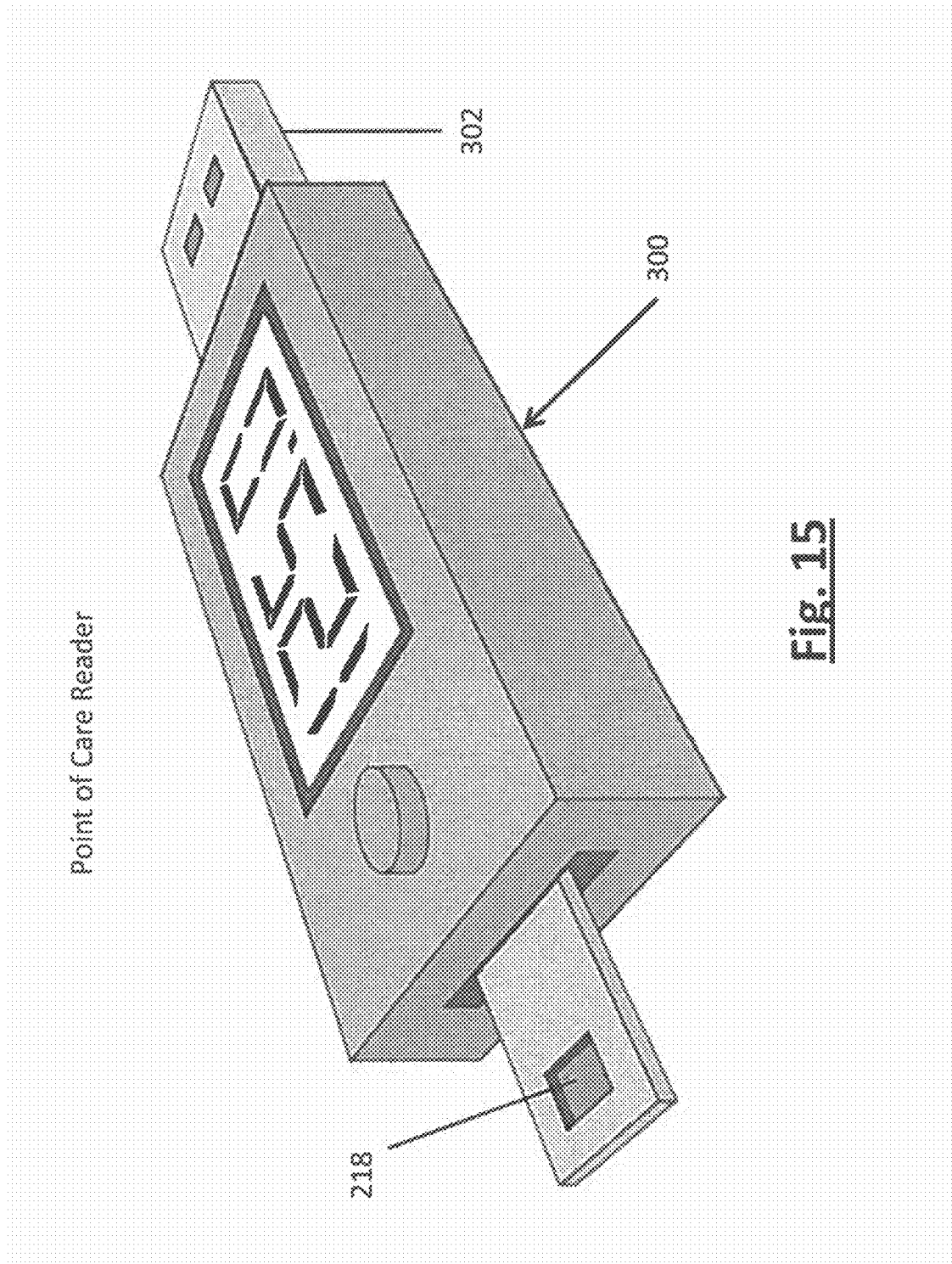
FIG. 15 is schematic of a point of care reader in accordance with the present invention.

In another implementation the sample/reagents are delivered to the thermally isolated reaction zone utilizing a thermally decoupled channel architecture as shown in FIGS. 12-15. FIG. 12 shows the cross section of this device. The thermal reaction zone 212 is enclosed by utilizing two thin membrane structures 208 spanning an opening in the support structure 204. The materials for the thin membranes 208 are chosen to have a low thermal conductivity to thermally insulate the thermal reaction zone. The distance between the two support structures 204 is kept on the order of 100 micron and the channel 218 is quasi two dimensional to minimize the thermal load. It extends to the sample loading area and sample is loaded into the thermally isolated zone 212 through capillary action along the fluid flow channel 218. The support structures 204 are separated for example by photolithographically defined polymer stand-offs 208. The membranes 208 on both support structures 204 are aligned using a lock and key structure so that the membranes 208 are facing each other to generate the thermally insulated reaction zone 212. The reaction zone 212 may contain one or multiple surfaces, which could be functionalized with various reagents as discussed above and below. The functionalized surfaces contain elements, a thermopile 206, to sense temperature changes and determine the heat of reaction between the analyte in the sample and the capture reagent. The capture reagent can be immobilized on one or more of the surfaces. Temperature sensors can be arranged to measure temperature changes differentially from two or more functionalized surfaces 222 as shown in FIG. 13. The thermally insulated zone 212 effectively contains two calorimeters. In FIG. 13 the thermopiles 206 are arranged such that thermoelements "hot and cold" junctions extend from one surface to the other to sense the temperature difference between reactions taking place on the two functionalized surfaces 222. One functionalized surface will act as control or reference. This has distinct advantages in that for example the heat of dilution can be eliminated from measurements by coating only one of the two surfaces with the capture reagent. The small microcalorimetry device size, capillary filling using a microchannel 218 and the simple assay heat signal-to-voltage readout can be used to miniaturize the thermal ELISA for use as an inexpensive, easy-to-use point of care device. This design does not require digital microfluidics or the merging of droplets on the calorimeter surface. The device includes readout contacts 210 connected to the thermopiles 206. The functionalized surfaces 222 can include enzyme linked to the capture reagent. A suspended membrane area 216 is used to form the reaction zone 212 and to contain the thermopile 206. Interlocking membranes 220 can keep structures aligned. The samples moves down the fluid flow channel 218 by capillary action alone. In this system, one way to determine the level of analyte is to slowly infuse in reagent for the enzyme linked to the secondary capture reagent bound to the analyte which is specifically bound to a selective region of the thermopile. Then one can compare the heat being measured from a functionalized region having the analyte with the heat from a non-functionalized region. As you infuse in the enzyme reagent you will initially get a spike in heat and then a new steady state raised level of heat as the enzyme kinetics reach steady state due to continued infusion of the enzyme reagent. The new steady state level is then compared to the temperature level from non-functionalized regions. In FIG. 15 a very schematic figure of a point of care reader using the device shown in FIGS. 12-14 is shown in a stylized reader 300. The device is inserted into the reader 300 and a sample is deposited in the fluid flow channel 218. The sample is then pulled by capillary action into the reaction zone 212 and the generated thermal response is read out as shown in the schematic as a reading of 125.0 for illustration purposes only. The point of care reader can include a USB charger plug 302 as known for current blood glucose readers.

Depending upon the intended application, the calorimeter 10 can be configured as a microcalorimeter or a nanocalorimeter. Advantageously, the calorimeter 10 is a simple, inexpensive, rapid, rugged, and field-deployable device architecture that can be used under a variety of conditions and settings, such as point-of-care environments. Unlike conventional point-of-care biochemical assays, which often include fragile and expensive optics, the calorimeter 10 of the present disclosure is comprised of a thin membrane with low thermal conductivity and a thin film thermopile structure or other thermal sensors capable of detecting pico- and femtograms of analyte in the sample (e.g., less than 100 picogram/milliliter) without the need for such optics at timescales of minutes. Due to the small thermal mass and the small footprint the reaction/detection is fast and typically not diffusion limited.

In one aspect, as shown in FIGS. 1 and 2, the support structure 12 comprising the calorimeter 10 can have a single or multi-layer configuration. In some instances, one or more layers comprising the support structure 12 can include a light-sensitive material, such as an epoxy-based negative photoresist (e.g., Su-8) to form the membrane responsible for the thermal insulation and/or defining the space between the layers containing the sample/reaction droplets and/or the support structure enclosing the device 20. The device 20 can also include a port 15 to allow for introduction of sample to the reaction zone 14. As described below, different components of the calorimeter 10 can be patterned on and/or integrated within the support structure 12. The support structure 12 can be prepared using conventional microfabrication techniques, such as those described in the Examples below. One example of a multi-layered structure 12 is illustrated in FIG. 2. Each layer of the support structure 12 can be identically or differently dimensioned when compared to other layers of the support structure 12. Although the support structure 12 is illustrated in FIG. 1 as having a rectangular configuration, it will be appreciated that other shapes are possible (e.g., circular, triangular, etc.).

In another aspect, the calorimeter 10 can include a hermetically-sealed and thermally decoupled central reaction zone 14 associated with the support structure 12. By "hermetically-sealed and thermally insulated", it is meant the area defined by the central reaction zone 14 forms an airtight seal sufficient to physically isolate and thermally separate the central reaction zone 14 from the ambient environment and temperature. The thermal insulation can also be achieved using two support structures 12 and 204 with two membranes sandwiched together and the fluid droplet connecting the two membranes while being thermally decoupled from the support structures 12. The spacing between the two membranes is formed using a thin spacing layer on either support structure. By "thermally decoupled", it is meant that a central reaction zone 14, 212 (discussed below) is thermally insulated from the support structure 12 and the ambient environment. Advantageously, since the calorimeter 10 measures the temperature rise in the central reaction zone 14, 212, the thermally decoupled central reaction zone 14 provides a highly accurate environment in which to measure thermal variation since there is little or no leakage of heat, especially when compared to a system where the heat is sunk to a reservoir.

As shown in FIGS. 1-2, the central reaction zone 14 is defined by a portion of the support structure 12, at least one temperature sensor is disposed on a surface of the support structure 12 (not shown in detail), and a sealing mechanism 20 such as a glass lid seals the central reaction zone 14. In some instances, the temperature sensor in the central reaction zone 14 can comprise a thermopile, a resistive temperature transducer, a thermal radiation detector, or a semiconducting temperature transducer. In other instances, the temperature sensor and/or a support structure surface defining the central reaction zone 14 can be at least partially coated or functionalized with a capture reagent or a labeling agent leading to a thermal signature when it comes in contact with the sample containing the analyte. In one example, a surface of the temperature sensor can be coated with a material (e.g., gold) to promote attachment or coupling of a capture reagent thereto to functionalize the surface of the central reaction zone 14. In some instances, the sealing mechanism 20 can include a glass cover or a drop of oil.

In another implementation the thermally decoupled central reaction zone 14, 212 can additionally or optionally include one or more capillary or membrane-sealed ports (not shown) that is/are in fluid communication with the central reaction zone 14, 212 and that permit introduction of a fluid sample into the central reaction zone 212 FIGS. 12-15. The capillary action with appropriate surface coatings in the reaction zone promotes rapid wicking of the sample into the space between the two membranes. Since the dimensional of the capillary port can be kept small evaporation is minimized. To enhance wicking the space in the thermally decoupled reaction zone 14, 212 can be filled with a fibrous material. The fibrous material could be coated with the detection agent thereby enhancing sensitivity by increasing the available surface to bind the detection agent.

Furthermore, the calorimeter 10 can include a capillary port (or ports) in fluid communication with other components of the calorimeter, so long as fluid samples can be introduced into the calorimeter and ultimately disposed or located within the central reaction zone 14, 212.

In another aspect, the support structure 12 can include at least one droplet transport region 16 associated therewith. The droplet transport region 16 can be configured to introduce a sample droplet onto the precoated reaction zone 14 or to merge the reagent droplet with a sample droplet comprising the fluid sample to form a reaction droplet in the central reaction zone 14. In some instances, the droplet transport region 16 comprises a digital microfluidic array that is free of any microfluidic channels or external pumps. Digital microfluidics is based on the concept of electro-wetting of liquid droplets on a dielectric surface (EWOD). Under an applied electric field, droplets experience a reduction in surface tension in the area of the electric field. Surface tension then drives the droplets towards the area of highest surface energy. Advantageously, this effect is exploited by the present disclosure to control droplet movement electronically without the need for microfluidic channels or external pumps.

Figure 3:
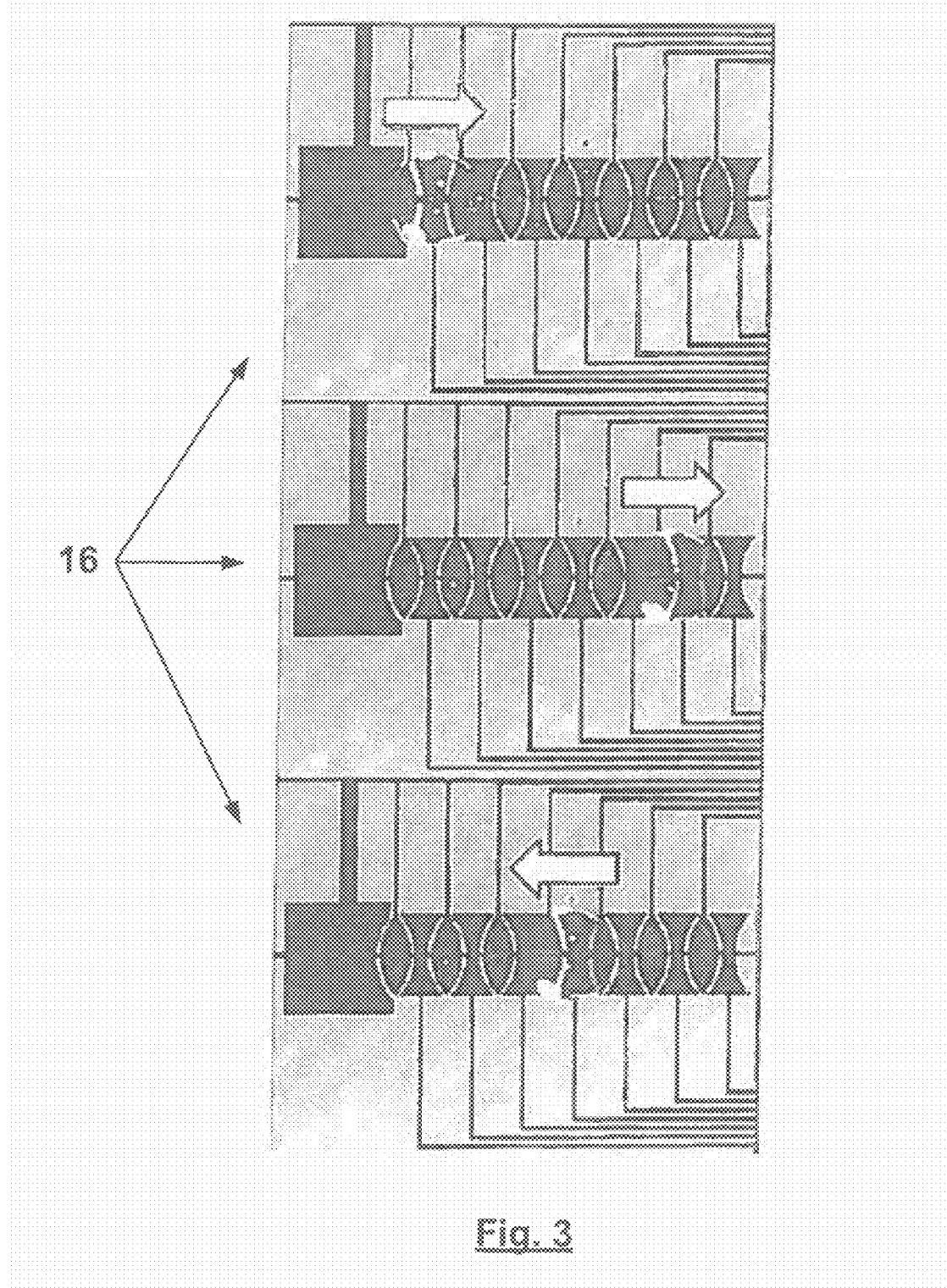
FIG. 3 is a series of photographs showing motion of a 10 nL droplet across a digital microfluidic array comprising the calorimeter in FIG. 1.

Each droplet transport region 16 can extend between the central reaction zone 14 and a loading area 22 where a reagent droplet can reside or be initially deposited. As shown in FIG. 3, each droplet transport region 16 can comprise a series of individual electrode pads arranged in a track or channel-like configuration. The calorimeter 10 can be connected to a programmable multichannel high voltage switch (not shown) to implement drop motion and/or droplet splitting. It will be appreciated that the calorimeter 10 can have any number of droplet transport regions 16, depending upon its intended use. As shown in FIG. 1, for example, the calorimeter 10 can include only a single droplet transport region 16 configured to merge a reagent droplet with a sample droplet located in the central reaction zone 14. In this instance, the sample droplet can be deposited directly into the central reaction zone 14, whereafter all or only a portion of the reagent droplet can be guided towards the central reaction zone via the droplet transport region 16. In another example, a calorimeter 10', FIG. 4 can include a droplet transport region 16 configured to merge a reagent droplet with a sample droplet in the central reaction zone 14, as well as a second droplet transport region 16' configured guide all or only a portion of the sample droplet to the central reaction zone. In other words, the sample droplet can first be deposited in a loading area 22 and then urged via the second droplet transport region 16' to the central reaction zone 14.

One or more of the droplet transport regions 16 can include a staging area 24 where a droplet (e.g., a reagent droplet or a sample droplet) can be heated or cooled. The staging area(s) 24 can be located between the central reaction zone 14 and a loading area 22 of a droplet transport region 16. In some instances, a staging area 24 can be located directly on the central reaction zone 14 or between the central reaction zone 14 and a loading area 22 configured to receive the sample droplet. In such instances, all or a portion of the sample droplet can be urged along the droplet transport region 16 until it is directly over or adjacent (e.g., in direct contact with) the staging area 22. In the staging area 22, the sample droplet can be heated to a desired temperature and for a period of time sufficient to prevent or mitigate serum matrix effects, for example.

In another aspect, the calorimeter 10 can include detection electronics 18 that are in electrical and/or thermal communication with the central reaction zone 14 and associated with the support structure 12. Detection electronics 18 can include electrical components, such as wires, capacitors, resistors, sensors, amplifiers, power sources, and the like, that may be needed for operation of the calorimeter. Detection electronics 18 can be disposed on or within the support structure(s) 12 comprising the calorimeter 10.

Figure 4:
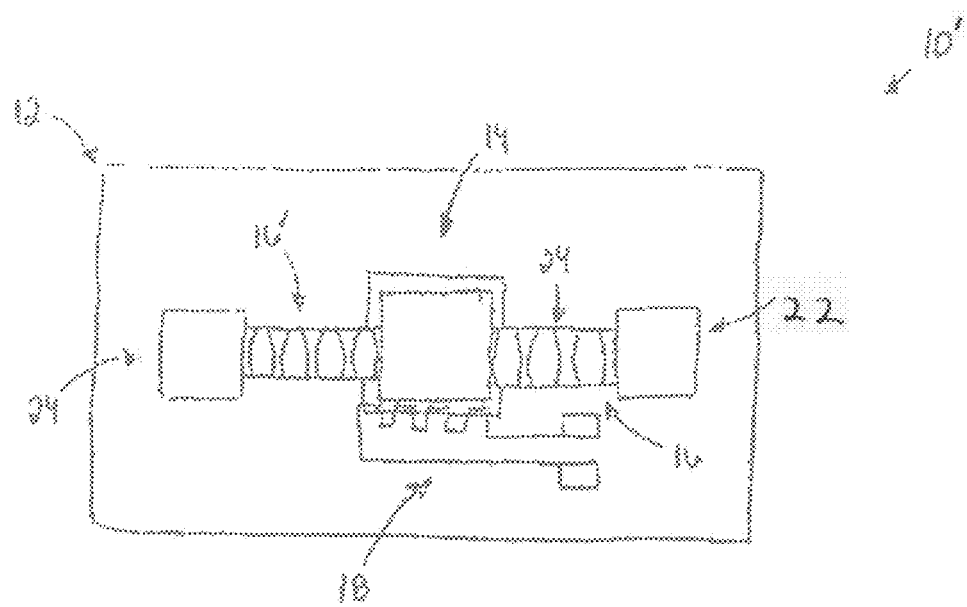
FIG. 4 is a top view showing an alternative configuration of the calorimeter in FIG. 1.

One example of a calorimeter 30 according to the present disclosure, referred to hereafter as the "Thermal ELISA", is illustrated in FIG. 4. Conventional ELISAs use enzyme-conjugated reagents, chemical substrates, and color developers to produce a visible or fluorescent signal that is converted—using a relatively expensive optical system—to an electronic signal indicative of analyte concentration. As described below, the Thermal ELISA 30 advantageously permits point-of-care analyte detection by detecting a heat of reaction generated either during direct binding of a capture reagent to the analyte of interest in the sample and/or an amplification step using an enzyme-substrate reaction in combination with a micromachined calorimeter with a small thermal mass using nanoliter-sized reaction volumes. Heat is detected in the reaction zone 14 using thin film thermocouples arranged in thermopiles to produce an electronic signal directly related to the analyte concentration. Using voltage generated by thermocouples to quantify the heat generated from direct binding between the capture reagent and analyte or an amplification step using a second capture reagent linked to an enzyme and a substrate reaction to enhance the heat signature, the Thermal ELISA 30 advantageously provides real-time data while also being inexpensive to make.

As shown in FIG. 5, one implementation of Thermal ELISA 30 can comprise a support structure 12, a sealed, thermally decoupled central reaction zone 14 associated with the support structure 12, a sample droplet transport region 32 associated with the support structure 12, a first droplet transport region 34 associated with the support structure 12, a second droplet transport region 36 associated with the support structure 12, and detection electronics 18 in electrical and/or thermal communication with the central reaction zone 14 and associated with the support structure 12. The central reaction zone 14 can include a temperature sensor and a functionalizable surface which can be at least partially coated with a capture reagent that specifically binds a target analyte. The device is sealed using another support structure 12 with a thin membrane aligned with the thin membrane on the first support structure 12 to generate a thermally isolated reaction zone 14 preserving the sensitivity of the device by using a sandwiched construction of thermally isolated membranes and support structures 12.

In another implementation the droplet transport regions can be on the support structure 12 sealing the device. Having the droplet transport regions 32, 34, 36 on the opposite side of the thermopiles will reduce a potential electrical cross talk between the thermopiles and the transport regions.

The support structure 12 comprising the Thermal ELISA 30 can have a single or multilayer configuration. For example, the support structure 12 comprising the Thermal ELISA 30 can be configured as shown in FIG. 5B. In this multilayer configuration, a base or lower portion 38 of the Thermal ELISA 30 can include a temperature sensor made of a Bi/Ti thermopile. A second layer 40 (e.g., Su-8) is placed on top of the lower portion 38. The layers 40 and 38 are thin to establish a thermally insulated central reaction zone 14. A gold pad 42 or any other surface coating can be disposed or patterned on top of a portion of the Su-8 membrane 40. Selectively applying gold or other suitable coatings to the thin membrane in the central reaction zone 14 permits capture of fixed amount of reagents in well-defined areas of the support structure 12, thereby providing a less volume sensitive assay and allowing bulk loading of the Thermal ELISA 30 during manufacturing. At least part of a major surface of the gold pad 42 can be coated with a capture reagent, such as an antibody. The central reaction zone 14 can thus include a cavity 44 defined by the support structure 46, the Su-8 membrane 40, and a second support structure which is in the simplest case a glass slide 43. A capillary port as shown at 15 in FIG. 2 or other structure can be used for introducing a sample droplet into the central reaction zone 14 and may extend through the second support structure (e.g., directly adjacent the central reaction zone). In this case, the second support structure would include a membrane to thermally insulate the central reaction zone 14.

The droplet transport regions 32-36 can be arranged on the support structure 12 as shown in FIGS. 4 and 5. For example, the sample droplet transport region 32 can extend between a sample loading area 48 and the central reaction zone 14, the first droplet transport region 34 can extend between a first reagent droplet loading area 50 and the central reaction zone, and the second droplet transport region 36 can extend between second and third reagent droplet loading areas 52 and 54. The droplet loading areas 50, 52, 54 each constitute a reservoir for one of the reagents and/or wash solutions. Selectively applying voltages to the reservoirs and the transport regions allows the dispensing of nanoliter sized droplets into the droplet transport region. The second and third droplet transport regions 34 and 36 can intersect one another at a common junction 56, which allows the first, second, and third reagent droplets to be selectively merged with the sample droplet to form a reaction droplet in the central reaction zone 14. Each of the droplet transport regions 32-36 comprises a digital microfluidic array based on EWOD.

In one example, the Thermal ELISA 30 can have a closed design in which the temperature sensor and the digital microfluidic arrays are fabricated independently on their own substrate but integrated together by placing the two halves together. In such instances, the upper support structure needs to provide a thermally insulated region above the reaction zone. The fluid in the reaction zone would span across both support structures. A heat flow model of the complete device can be constructed to find the optimal membrane and thermopile configuration. The EWOD control pads comprising each microfluidic digital array can occupy the bottom or lower half, while the temperature sensor (e.g., thermopile) can be patterned on the top or upper half. For example, the EWOD layer would need to be fabricated on a freestanding Su-8 membrane (as is done for the temperature sensor) to reduce heat transfer to the support structure. To allow for visualization of the droplets during transport, the EWOD layer can be fabricated on a transparent support structure.

In one implementation of the calorimeter device the reaction zone contains a thin film resistor, not shown, which allows a well-defined amount of heat to be generated directly in the reaction zone 14 for calibration purposes and to provide a means to heat the reaction zone 14 to eliminate nonspecific binding to mitigate matrix serum effects as described in the present specification. Alternatively, the heating could be accomplished using a pulsed laser.

In some instances, the sample droplet transport region 32 can include a staging area 24 where a droplet containing sample can be heated as described above. Furthermore, the staging area 24 could also contain a functionalized surface e.g. a coated gold surface or a capture reagent to capture an interfering analyte, which facilitates selective binding of interfering analytes before the droplet is moved onto the reaction zone 14. In this case the staging area 24 acts as a pull down assay extracting one or more analytes from the sample droplet. The staging area 24 can be located within the sample droplet transport region 32 between the central reaction zone 14 and the sample loading area 48. It can also be located directly in the reaction zone 14, not shown. All or a portion of the sample droplet can be urged along the sample droplet transport region 32 until the sample droplet is directly over or adjacent (e.g., in direct contact with) the staging area 24. In the staging area 24, the sample droplet can be heated to a desired temperature and for a period of time sufficient to prevent or mitigate serum matrix effects.

In another aspect, the support structure 12 for Thermal ELISA 30 can include detection electronics 18 that are in electrical and/or thermal communication with the central reaction zone 14. Detection electronics 18 can include electrical components, such as wires, capacitors, resistors, sensors, amplifiers, power sources, and the like, that may be needed for operation of the Thermal ELISA 30. Detection electronics 18 can be disposed on or within the support structure(s) 12 comprising the Thermal ELISA 30.

Detection Methods

Figure 6:
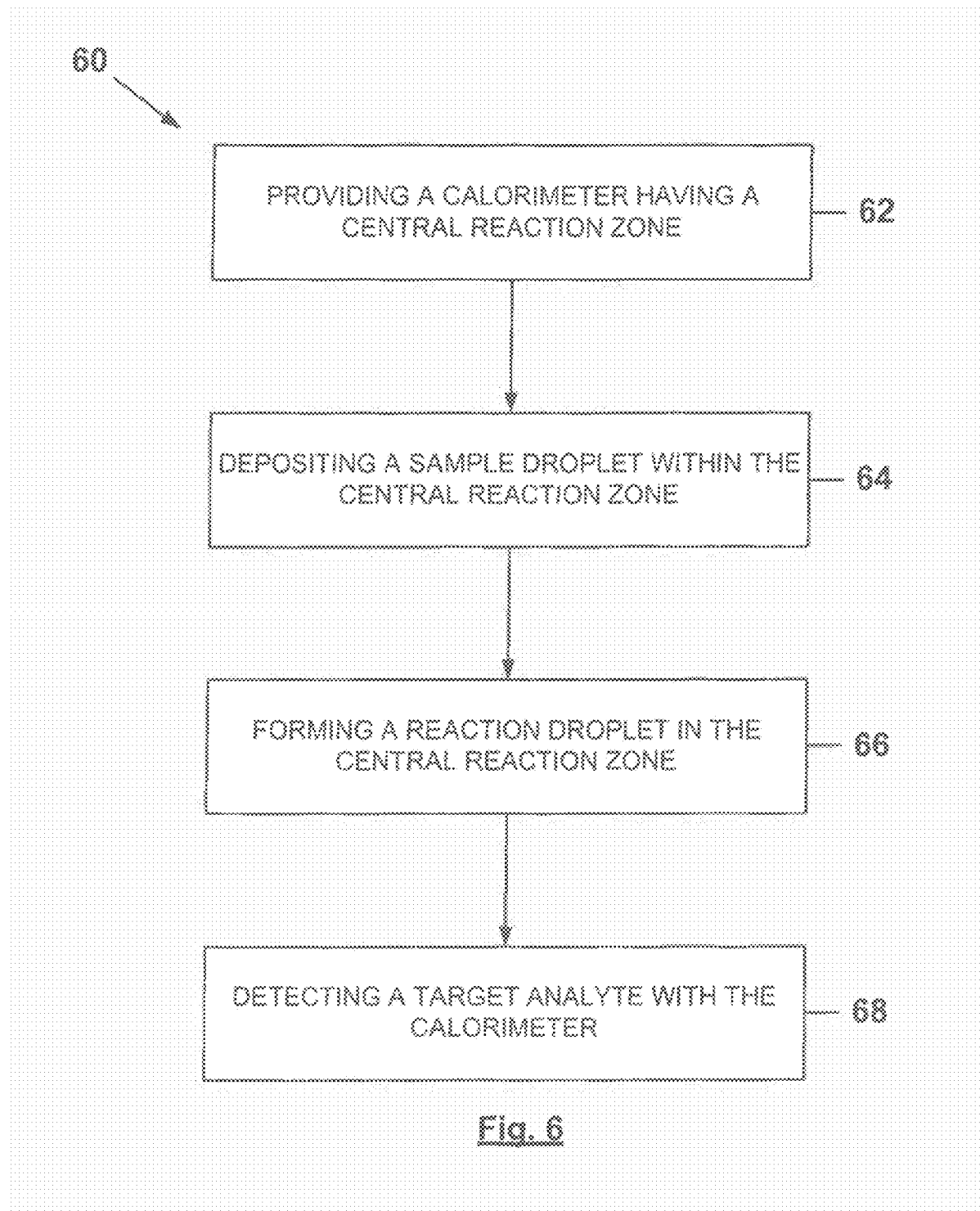
FIG. 6 is a process flow diagram illustrating a method for detecting a target analyte in a fluid sample according to another aspect of the present disclosure.

Another aspect of the present disclosure can include a method 60 FIG. 6 for detecting a target analyte in a fluid sample. The method 60 can generally include the steps of: providing a calorimeter having a thermally insulated central reaction zone where the ratio between thermal mass $C_{tot}$ and total thermal conductance $G_{tot}$ is on the order of less than 1 second for tau (Step 62); depositing a sample droplet within the central reaction zone (Step 64); forming a reaction droplet in the central reaction zone (Step 66); and detecting a change in temperature over time which can be used to determine the concentration of target analyte in the sample droplet with the calorimeter (Step 68).

In another implementation the calorimeter can contain a functionalized surface which is coated with the capture agent and the sample can be directly deposited into the reaction zone. This implementation of the method does not require any digital microfluidics. The capture agent could include secondary reactions leading to an amplification of the heat generated during the chemical reaction of sample with the capture agent.

The method 60 can find use in a variety of diagnostic applications and point-of-care environments including, but not limited to, healthcare, agriculture, industry, military, and homeland security. Current point-of-care diagnostic devices and methods cannot detect target analytes (e.g., pathogens, biomarkers, chemical and biological warfare agents) within very short periods of time (e.g., within minutes) at high levels of sensitivity and specificity. Furthermore, existing diagnostic devices and methods are very expensive for the equipment and per test, require a laboratory or hospital setting, highly trained technicians, expensive infrastructure, and from hours to days to get the results.

As described in more detail below, the method 60 of the present disclosure overcomes the drawbacks of conventional diagnostic platforms and associated methods by providing a fast and efficient platform that provides point-of-care results in a short period of time (e.g., less than 10 minutes) with high sensitivity and specificity at least by virtue of its ability to detect heat in pico-joules. This pico-joule sensitivity yields the results in speed, sensitivity, specificity, and cost needed and lacking in present diagnostics. Additionally, unlike conventional diagnostic methods, the method 60 of the present disclosure can be performed in extreme conditions by personnel with little training.

Referring to FIG. 6, one step of the method 60 can include providing a calorimeter 10 (Step 62). In one example, the calorimeter 10 used for the method 60 can be identically or similarly constructed as the calorimeter shown in FIG. 1 and described above. Thus, the calorimeter 10 can comprise a support structure 12 having a thermally insulated central reaction zone 14 where the ratio between thermal mass $C_{tot}$ and total thermal conductance $G_{tot}$ is on the order of less than 1 second for tau, a second support structure 12 sealing the reaction zone while providing thermal insulation, at least one droplet transport region 16 associated with the support structure 12, and detection electronics 18 in electrical and/or thermal communication with the central reaction zone 14 and associated with the support structure 12.

At Step 64, a sample droplet can be deposited within the central reaction zone 14. The sample droplet can be suspected of containing one or more target analytes, and can be obtained from a variety of sources. In one example, the sample droplet can include a biological sample that has been previously withdrawn from a subject (e.g., blood, serum, saliva, etc.) or a cell culture system (e.g. culture media). In another example, the sample droplet can include an environmental sample (e.g., polluted water) suspected of containing one or more target analytes. A desired volume of the sample droplet can be loaded into the calorimeter 10. In one example, the volume of the loaded sample droplet can be nanoliter-sized, preferably 100 nanoliters or less. The sample droplet can be loaded into the calorimeter 10 via a capillary port or membrane-bound port. In some instances, the sample droplet can be loaded through a capillary port 218 directly into the central reaction zone 14. In other instances, the sample droplet can be loaded onto the loading area 22 associated with the droplet transport region 16. In such instances, all or a portion of the sample droplet can be guided to the central reaction zone 14 via the microfluidic digital array comprising the droplet transport region 16. As described above, this can be achieved by applying an electric potential to the control pads of the droplet transport region 16 in an amount and for a time sufficient to change the degree of hydrophilicity of the sample droplet and thereby cause all or part of the sample droplet to advance to the next control pad towards the central reaction zone 14.

Once the sample droplet has been loaded into the calorimeter 10, a reagent droplet can be merged with the sample droplet in the central reaction zone 14 to form a reaction droplet (Step 66). This can be achieved by applying an electric potential to the droplet transport region 16 in an amount and for a time sufficient to change the degree of hydrophilicity of the reagent droplet and thereby cause all or part of the reagent droplet to advance towards the central reaction zone 14. In one example, the reagent droplet can be nanoliter-sized, preferably 100 nanoliters or less. In another example, each of the sample droplet, the reagent droplet, and the reaction droplet can be nanoliter-sized, preferably 100 nanoliters or less. In some instances, the reagent droplet can contain one or more capture reagents that specifically bind to and/or react with the target analyte(s) which concentration and/or presence is determined. In other instances, the reagent droplet can contain one or more detection elements (e.g., labeling agents, reactive moieties, reaction substrates). In such instances, one or more capture reagents may at least partially coat a surface of the central reaction zone 14. It will be appreciated that, in some instances, it may be desirable to heat the sample droplet prior to formation of the reaction droplet. In such instances, the sample droplet can be positioned about a staging area 24 and heated for a time and at a temperature sufficient to prevent or mitigate any serum matrix effects.

Upon formation of the reaction droplet, a heat of reaction is produced or generated by the interaction of the target analyte (if present) and the capture reagent. Using the temperature sensor of the calorimeter 10, heat generated is detected as temperature difference between the reaction zone 14 and the support structure 12 which produces an electronic signal (a potential difference or voltage) indicative of target analyte concentration. Heat detection, and thus determination of the target analyte in the fluid sample, can be calculated using, for example, the methods described by Xu et al., Anal Chem. 80, 2728-2733 (2008) and Lubbers et al., Anal Chem. 83, 7955-7961 (2011). To extend the dynamic range of the method 60, the digital microfluidic arrays can be controlled to repeatedly pass small volumes (e.g., nanoliter-sized) of the sample droplet through the central reaction zone 14 to determine the concentration of the target analyte without driving the capture reagents into saturation.

In instances where the heat of reaction is generated by an enzyme-catalyzed reaction, the reaction can be repeated multiple times by bringing in new reagents (e.g., reaction substrates) to increase sensitivity. Since the enzyme is not consumed in such a reaction, this leads to amplified heat production and thus signal generation.

It will be appreciated that the method 60 can find use in a variety of assays and applications including, but not limited to the following.

Polymerase chain reaction (PCR)—PCR relies on thermal cycling of cycles of repeated heating and cooling of the reaction for DNA melting an enzymatic replication of the DNA. Primers containing sequences complementary to the target region along with DNA polymerase are key components to enable selective and repeated amplification. As PCR progresses, the DNA generated is itself used as a template for replication, setting in motion a chain reaction in which the DNA template is exponentially amplified. PCR can be extensively modified to perform a wide array of genetic manipulations. The calorimeter and method of the present disclosure permits rapid heating of samples (e.g., by way of laser-emitting diodes or resistors) to rapidly cycle the temperature of the samples not only enabling PCR but also being able to detect the onset of the chain reaction utilizing the temperature signature of the reaction. The nanoliter-sized volumes used as part of the method 60 allow for almost instant heating and cooling of the droplets and, thus, the temperature cycles needed for PCR;

Antibiotic analysis—the method 60 can be used to evaluate a complete panel of antibiotics against a given bacterium to determine which antibiotic is most effective by, for example, monitoring cessation or alteration of cellular activity as determined thermally when the correct antibiotic is applied. This can also find use in determining whether a given bacterium is drug resistant. Further, since it is known that bacterial enzymes can break down antibiotics, the method 60 can be used to detect a thermal signature when a bacterium producing a particular enzyme is contacted with a particular antibiotic;

Chemotherapy agents—the method 60 can find use in determining the correct chemotherapy agent for use against specific types of cancer. For example, a panel of chemotherapy agents can be screened against particular cancer cells to determine the effect on cancer cell activity. The cessation or alteration of cancer cell activity and thus thermal signature can be used to identify optimal chemotherapy agent(s) (or lack of one) without subjecting the subject to the side effects of trial and error;

Drug screening—the pharmaceutical industry is constantly looking for new small molecule drugs to treat disease. Many new drug candidates are screened to determine if they are chemically-modified by P450 enzymes (so-called because they absorb light at a wavelength of 450 nanometers). These enzymes are present in the human liver and can metabolically alter drugs given to human patients. Additionally, microbes (e.g., bacteria, fungi, etc.) produce similar enzymes. The P450 enzymes can be costly to purify and screen, so the method 60 of the present disclosure can be used to screen for new drug candidates and thereby decrease assay costs.

Pathogenic bacteria screen—pathogenic bacteria (such as some strains of *Staphylococcus aureus*) produce the enzyme catalase. The catalase enzyme test is one of the key biochemical tests used to characterize a bacterial infection. The bacterium is mixed with hydrogen peroxide. If the bacterium produces catalase, then hydrogen peroxide will be enzymatically decomposed. The method 60 of the present disclosure can be performed by mixing a bacterium with hydrogen peroxide (which produces bubbles) as well as a detectable amount of heat, which can be detected by the calorimeter 10.

Figure 7:
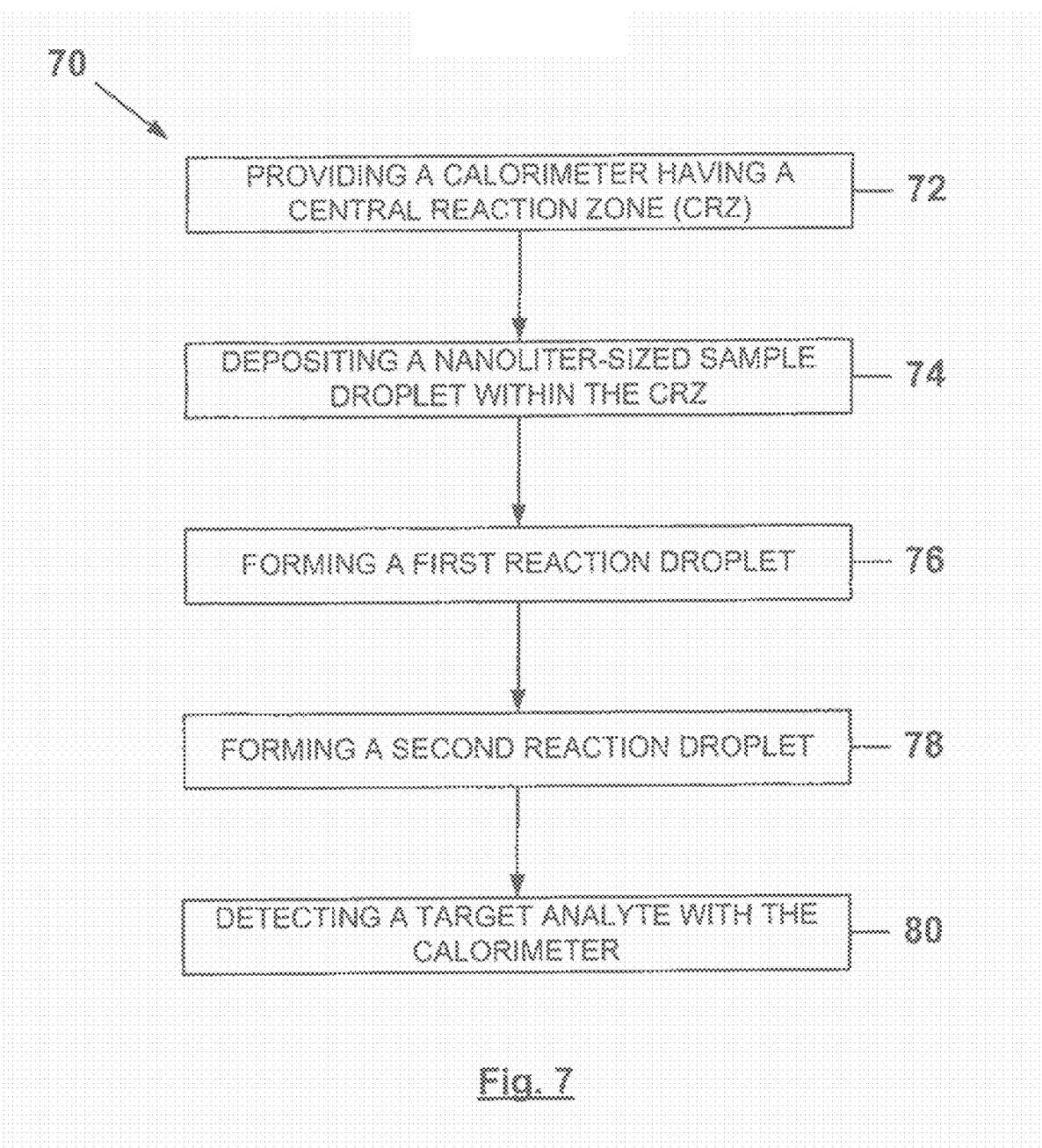
FIG. 7 is a process flow diagram illustrating a method for detecting a target analyte in a fluid sample in a point-of-care environment according to another aspect of the present disclosure.

Another aspect of the present disclosure is illustrated in FIG. 7 and includes a method 70 for detecting a target analyte in a fluid sample in a point-of-care environment. The method 70 can generally include the steps of: providing a calorimeter with low thermal mass/low thermal conductivity ratio and a functionalized surface in the center of the reaction zone as described above (Step 72); functionalizing the surface with at least partially one capture agent with a high affinity for the analyte to be detected; depositing a nanoliter-sized sample droplet within a central reaction zone of the calorimeter (Step 74); forming a first reaction droplet (Step 76); and detecting the heat generated through direct binding of the capture agent with the analyte of interest in the sample. The direct binding event leads to a difference in temperature, which is then used to determine the concentration of analyte in the sample. This method does not necessarily require the use of digital microfluidics and the calorimeter surface can be functionalized and stored prior to the exposure of the calorimeter surface with the sample. A subsequent wash step and the exposure of the surface to a sample with a known amount of analyte could be used to calibrate the device for determining the absolute analyte concentration.

In another implementation, instead of heat generated from direct binding the capture agent could also be any detection agent (e.g. enzyme A) and an analyte which react with each other (e.g. the corresponding substrate for enzyme A). Using this approach the concentration of chemical substrate in the sample droplet can be determined. A subsequent wash step and the exposure of the surface to a sample with a known amount of analyte could be used to calibrate the device for determining the absolute analyte concentration.

Figure 11:
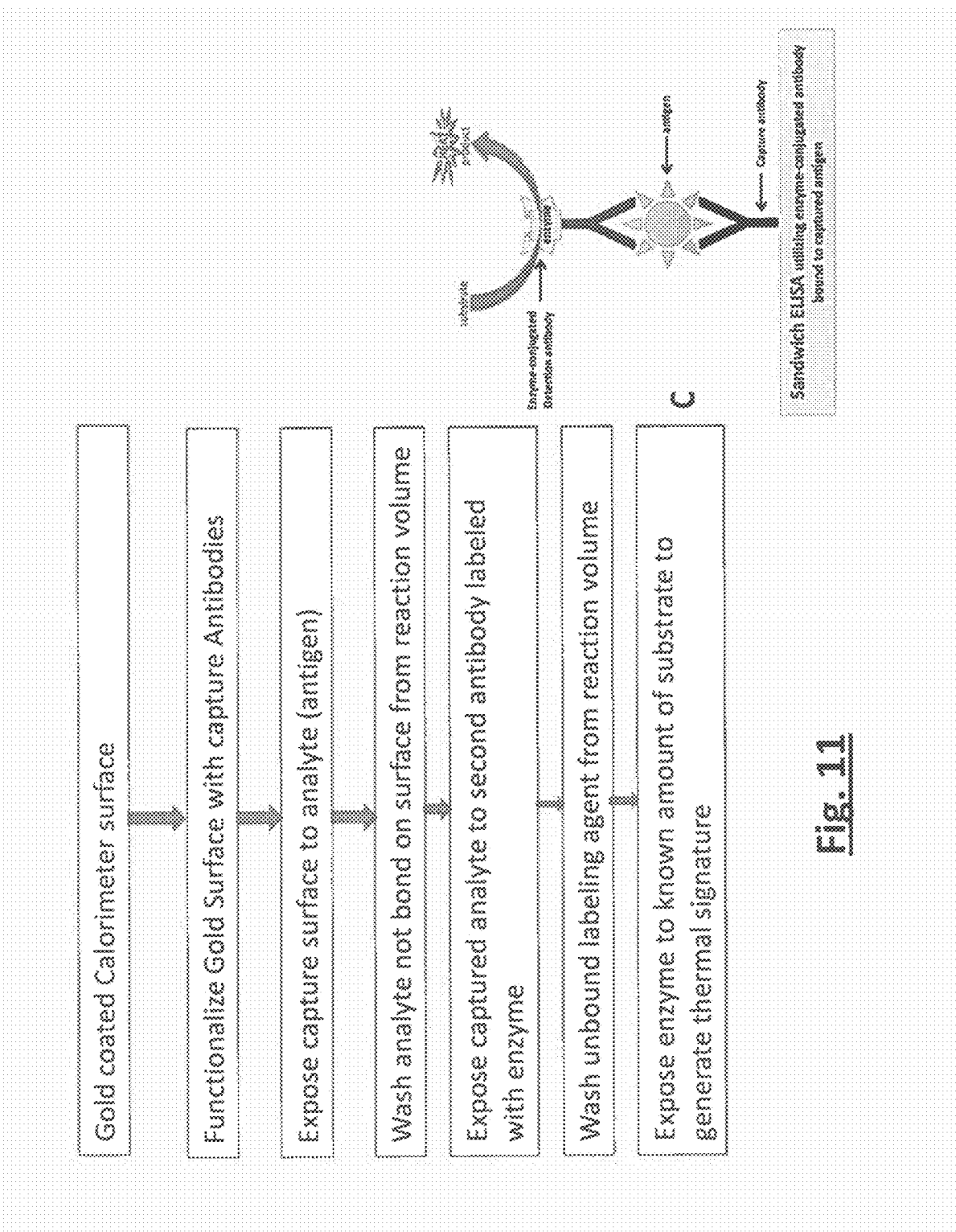
FIG. 11 is a flow chart illustrating another embodiment of the present invention.

In yet another implementation of the method FIG. 11 especially if the heat generated through direct binding is below the detection threshold an amplification step can be added to extend the sensitivity of the calorimeter assay. If the amplification step is added the method comprises the steps of: providing a calorimeter with low total thermal mass/low total thermal conductivity ratio on the order of 1 and a functionalized surface in the center of the reaction zone as described above (Step 112); functionalizing the surface partially with at least one capture agent with a high affinity for the analyte to be detected (Step 114); depositing a nanoliter-sized sample droplet within a central reaction zone of the calorimeter (Step 116); forming a first reaction droplet. In this step the sample analyte is immobilized on the functionalized calorimeter surface. Since we are working in nanoliter sized volumes the diffusion times are short. Multiple sample droplets could be guided over the surface to enhance capture of the sample analyte leading to concentrating of analyte on the surface. The process of enrichment benefits from a large surface to volume ratio in nanoliter sized droplets. The next step is a wash step removing any unbound analyte from the surface of the calorimeter (Step 118). During this step and the previous step, the reaction volume could be heated to eliminate unspecific binding and serum matrix effects as discussed above. After the wash step, a specific second capture agent is merged onto the reaction zone to bind a reaction moiety (e.g. enzyme) to the analyte immobilized onto the calorimeter surface (Step 120). A subsequent wash step removes unbound reaction moiety from the reaction zone (Step 122). The reaction moiety, enzyme, is now bound to the analyte immobilized onto the calorimeter surface. In the detection step the enzyme substrate is now deposited onto the calorimeter surface (Step 124). The moiety is selected to generate a large thermal signature when exposed to a specific reagent leading to an amplification and therefore expending the detection range of the calorimeter. If the moiety is an enzyme, which does not get consumed during the reaction the thermal signature could be regenerated exposing the calorimeter surface with multiple droplets containing substrate. The thermal signature can be used to determine the concentration of the analyte in the sample or to just provide a yes no response to the presence or absence of the analyte.

Current ELISAs are expensive to operate, expensive to maintain, and are slow. They require highly trained technicians and are relatively fragile. They are done in a laboratory setting with expensive reagents and take from hours to days to produce results. Also, conventional ELISAs use enzyme-conjugated reagents, chemical substrates, and color developers to produce a visible or fluorescent signal that is converted using a relatively expensive optical system susceptible to changes in the optical properties of the sample with the detection reagents to an electronic signal indicative of analyte concentration. The methods of the present disclosure, however, are advantageously based on measurement of heat generated by direct-binding events (e.g., label-free) or enzyme-conjugated reagents and enzyme substrates to amplify the signal (e.g., as in a conventional sandwich ELISA). As described below, the methods provide real-time data and uses voltage generated from a calorimeter to quantify the heat generated from direct binding or an amplification step using an enzyme-substrate reaction. Based on a model taking into account calorimeter characteristics, the known reaction enthalpy and enzyme activity, the heat generated can be used to directly determine the enzyme concentration and concomitantly the analyte concentration unaffected by the optical properties of the sample or electronic offsets. Advantageously, the nanoliter-sized volumes used with the methods limit sample and reagent diffusion times to seconds and thereby increasing assay throughput, multiplexing and sample consumption.

At Step 74 and 116, a nanoliter-sized sample droplet can be deposited within the central reaction zone 14. The central reaction zone 14 can include a temperature sensor and a surface at least partially coated with a capture reagent that specifically binds or reacts with the target analyte. The sample droplet can be suspected of containing one or more target analytes, and can be obtained from a variety of sources. In one example, the sample droplet can include a biological sample that has been previously withdrawn from a subject (e.g., blood, serum, saliva, etc.) or cell culture system (e.g. media). In another example, the sample droplet can include an environmental sample (e.g., polluted water) suspected of containing one or more target analytes. The sample droplet can be loaded into the Thermal ELISA 30 via a capillary or membrane-bound port that is in fluid communication with a loading area 48 of the sample droplet transport region 32. All or a portion of the sample droplet can be guided to the central reaction zone 14 via the sample droplet transport region 32.

In one implementation of the device this can be achieved by applying an electric potential to the sample droplet transport region 32 in an amount and for a time sufficient to change the degree of hydrophilicity of the sample droplet and thereby cause all or part of the sample droplet to advance towards the central reaction zone 14. The target analyte, if present in the sample droplet, can specifically bind to or react with the capture reagent upon transport of the sample droplet to the central reaction zone 14. Next, a first droplet comprising a labeling agent (e.g., an antibody that specifically binds to the target analyte) coupled with a reactive moiety (e.g., an enzyme) can be guided along the first droplet transport region 34 until the first droplet merges onto the reaction zone onto which the analyte has been immobilized (Step 76). This can be achieved by applying an electric potential to the first droplet transport region 34 in an amount and for a time sufficient to change the degree of hydrophilicity of the first droplet and thereby cause all or part of the first droplet to advance towards the central reaction zone 14. A third droplet comprising a wash solution (e.g., buffered PBS) can then be guided along the second droplet transport region 36, and part of the first droplet transport region 34, until the third droplet merges with the first reaction droplet and removes any unbound reactive moiety from the central reaction zone 14. This can be achieved by applying an electric potential to the second droplet transport region 36 in an amount and for a time sufficient to change the degree of hydrophilicity of the third droplet and thereby cause all or part of the third droplet to advance towards the central reaction zone 14.

At Step 78, a second droplet comprising a reaction substrate (e.g., specific to the enzyme comprising the reactive moiety) can be guided along a different portion of the second droplet transport region 36, and part of the first droplet transport region 34, until the second droplet merges with the first reaction droplet to form a second reaction droplet. This can be achieved by applying an electric potential to the second droplet transport region 36 in an amount and for a time sufficient to change the degree of hydrophilicity of the second droplet and thereby cause all or part of the second droplet to advance towards the central reaction zone 14. Upon the deposition of the second droplet onto the capture surface, the reactive moiety reacts with the reaction substrate and, in the process of doing so, generates or produces a heat of reaction.

Using the temperature sensor of the Thermal ELISA 30, heat is detected to produce an electronic signal a potential difference or voltage indicative of target analyte concentration (Step 80). Heat detection, and thus determination of the target analyte in the sample droplet, can be calculated using, for example, the methods described by Xu et al., *Anal Chem.* 80, 2728-2733 (2008) and Lubbers et al., *Anal Chem.* 83, 7955-7961 (2011). The method 70 can be repeated multiple times by bringing in new reagents (e.g., reaction substrates) to increase sensitivity. Since the reactive moiety (e.g., enzyme) is not consumed in the reaction, this leads to amplified heat production and thus signal generation.

Other advantages of the method 70, besides those described above, can also include the following use of nanoliter-sized volumes permits numerous (e.g., hundreds) of assays to be performed and thereby enhance signal-to-noise and allow multiple target analytes to be detected in a multiplexed, high-throughput rapid screening approach.

The absolute amount of bound enzyme label can be determined if the activity of the enzyme is known. In such instances, the Thermal ELISA 30 does not need any calibration and, thus, the assay can be performed to determine the activity of the enzyme just prior to the determination of the amount of bound enzyme label(s) with the assumption of Michaelis-Menten reaction kinetics.

When reactions take place over long time periods, the detection of small amounts of bound enzymes can be enhanced if, after a sufficient time, a known excess amount of enzymes is added to the reaction volume and the amount of heat generated is measured. The amount of chemical substrate turned over can be determined and subtracted from the amount of chemical substrate added after the initial enzyme labeling step resulting in the amount of chemical substrate turned over by the originally-bound enzyme labels. This way, drifts in the baseline can be eliminated which results in an enhanced sensitivity.

Multiple chemical substrate injections can be averaged to enhance the signal-to-noise ratio averaging multiple injections of chemical substrate over time.

The 1/e time constant can be directly used to determine the amount of enzyme labels bound, thereby simplifying quantification and enhancing enzyme specificity.

Signal gating can be used to eliminate crosstalk between the digital microfluidics and calorimeter signal amplification/processing.

The following examples are for the purpose of illustration only and are not intended to limit the scope of the claims, which are appended hereto.

Figure 5A:
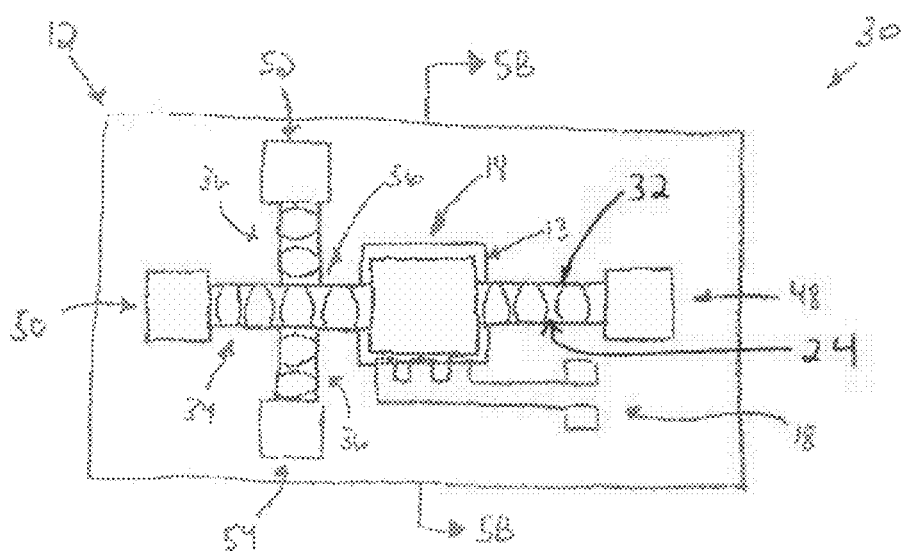
FIG. 5A is a top view showing another alternative configuration of the calorimeter in FIG. 1.

The overall goal of the Examples was to utilize nanocalorimetry to develop a quantitative rapid ELISA platform technology utilizing thermal readout strategies with picogram/milliliter sensitivity. FIGS. 5A-B represent one configuration of a nanocalorimeter (e.g., the Thermal ELISA 30) capable of point-of-care immunoassays with pictogram/milliliter sensitivities. The Thermal ELISA 30 was used to quantify HERCEPTIN antibodies (Genentech USA, Inc., San Francisco, Calif.) at therapeutic concentrations in human serum.

Example 1

When nanocalorimetry is used to measure the heat generated by an enzyme (e.g., HRP)-catalyzed reaction, the heat generated is proportional to the reaction's substrate (e.g., $H_2O_2$) concentration (FIG. 8) and the time course is determined by enzyme activity, reaction volume and intrinsic device characteristics. If we select the direct-binding of IgG to protein A as a benchmark and use 45 kJ/mole heat of reaction, a heat uncertainty of 1 nJ corresponds to an IgG detection limit of $45 \cdot 10^{-15}$ mole or the smallest mass of 720 pg based on a mass of 160 kDa for IgG. Although, there are biomarkers where a label free detection is feasible, we used HERCEPTIN (Genentech USA, Inc., San Francisco, Calif.) as an exemplar model system which requires an enzyme amplification step to extend sensitivities to therapeutic relevant concentrations.

Figure 8:
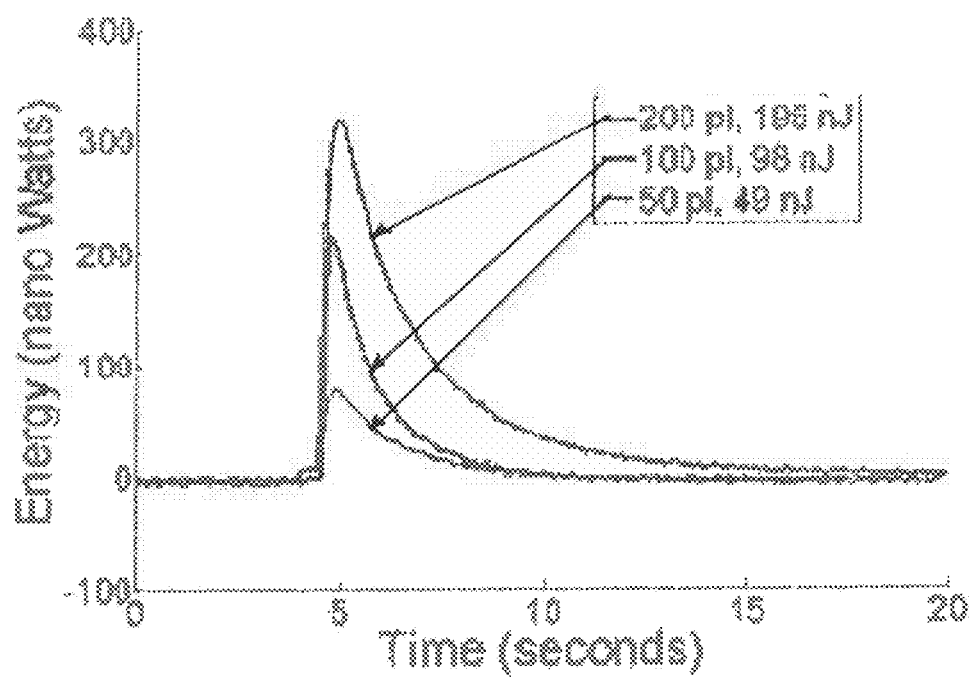
FIG. 8 is a graph showing an assay response, using a calorimeter of the present disclosure, for 100 pg of horse radish peroxidase (HRP) in 1 nanoliter upon the injection of 50, 100, and 200 picoliters of hydrogen peroxide.
Figure 9:
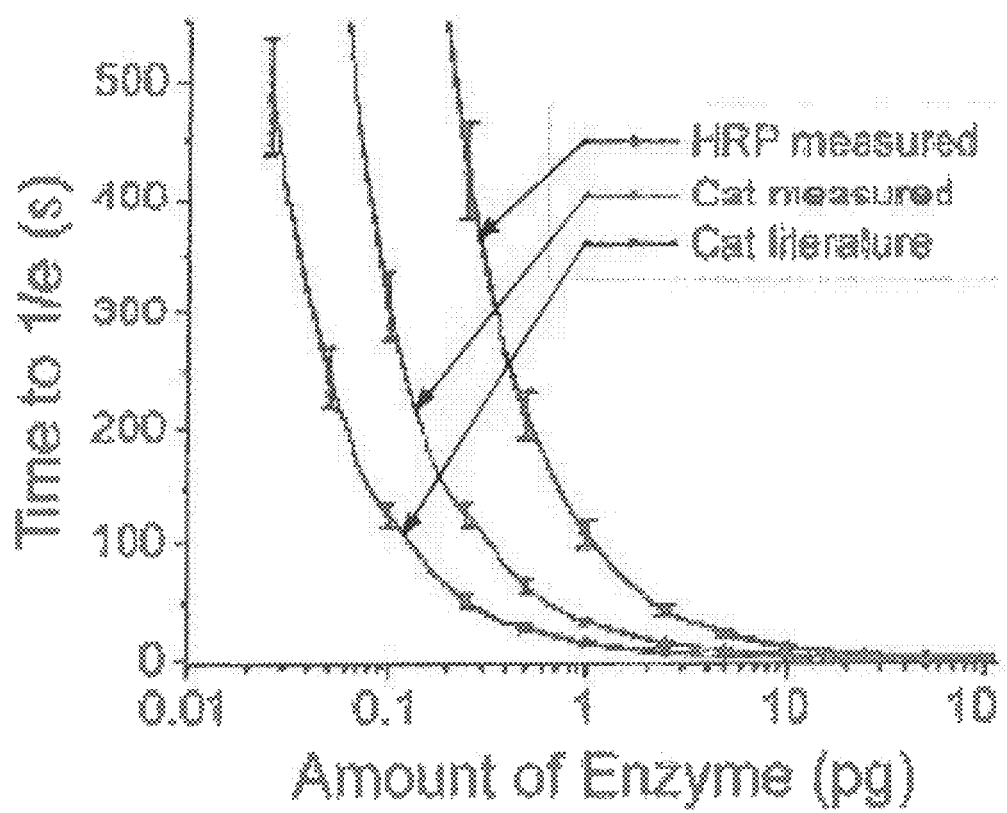
FIG. 9 is a graph showing assay sensitivity, using a calorimeter of the present disclosure, with HRP and catalase for enzyme amplification, the 1/e time is directly related to the enzyme concentration and the activity of the enzyme.

When HERCEPTIN (Genentech USA, Inc., San Francisco, Calif.) IgG is bound to the nanocalorimeter sensor surface and is detected using an HRP-conjugated anti-human IgG antibody and $H_2O_2$, our detection limit is <10 pg. The preliminary data, FIGS. 8-9, show that enzyme amplification increases the detection limit by at least 2-3 orders of magnitude. Currently, micropipettes are used to deliver sub nanoliter (nL) droplets to the sample on the surface of the nanocalorimeter. This approach is not ideal, is labor intensive and difficult to automate with limited fluid handling/routing capabilities.

Fluid handling and antigen/sample routing is achieved without the use of channels utilizing EWOD or digital microfluidics to move fluids across assay sensor surfaces encased in a hermetically-sealed environment, with samples being introduced into the device via capillarity using an easily penetrable port.

Digital microfluidics is based on the concept of EWOD. Under an applied electrical field, droplets experience a reduction in surface tension in the area of the electrical field. Surface tension then drives the droplets toward the area of highest surface energy. This effect can be exploited to control droplet movement electronically without the need for microfluidic channels or external pumps. FIG. 3 shows an actual sequence of imaged droplets demonstrating droplet movement along the pads of an EWOD track. Our drive electronics allowed us to move nanoliter (nL) droplets at pad transition rates of up to 50 Hz. EWOD can also be used to reliably split and combine drops thereby allowing sequences of wash, dilution, enrichment and downstream reactions to be performed all on a chip. The thermopile, Su-8 layers/membrane, and backside etch dimensions are all controlled by a photomask layout. The major fabrication steps and the flip chip assembly for the digital nanocalorimeter are described below.

Calorimeter Fabrication

Openings in the backside of a double-sided silicon nitride (SiN) coated Si <100> wafer are made first. Dry etching of SiN and patterning is carried out using Shipley's S1813 photoresist. The exposed Si is anisotropically etched in 30% w/w KOH at 80° C. The photoresist Su-8 2002 is spun onto the surface at 3000 rpm to generate a 2 μm thick Su-8 membrane layer (step 2). A 200 nm Ti layer is deposited using an Innotech e-beam deposition/ion-mill system and patterned with the S1813 (step 3). Next a 400 nm Bi layer is applied and patterned as in step 3 (step 4). This is thicker than the Ti due to the high resistivity of Bi and a direct increase in thermopile noise with resistance. A 100 nm silicon dioxide passivation layer is then applied to prevent oxidation and damage to the thermopile (step 5). Next a 10 nm gold (Au) layer is applied to provide the ground plane for the digital microfluidics (step 6). The contact pads are masked off during deposition during step. The SiN under the membrane is removed using Reactive Ion Etch (RIE) (step 7). The wafer is then diced and each chip sealed with a lid containing the digital microfluidics (step 8).

Digital Microfluidics Fabrication

The EWOD layer is also fabricated on a freestanding Su-8 membrane on a SiN support structure using the same techniques as above. The electrodes are patterned in Ti and an additional 2 μm Su-8 layer spun on top of the electrodes to form the dielectric layer. Reagent reservoirs are etched into the EWOD support structure at the same time as the freestanding Su-8 membrane is formed. The spacing of the reservoirs can be adapted to the 384 or 1536 micro-well format to make use of commercially available robotic liquid handlers for automated reagent loading.

Digital Nanocalorimeter Flip-Chip Assembly

Spacers to define the gap between the EWOD layer and the calorimeter are created using Su-8 in thicknesses ranging between 10 and 50 μm. Then, 1% Teflon AF (DuPont) is spun on at 1000 rpm to form a hydrophobic layer. This is baked at 260° C. to dry and reflow the fluoropolymer and seal the device. Reagent is loaded into reservoirs and covered by oil to prevent evaporation and hermetically seal the device. The device is connected to a programmable multi-channel high voltage switch to implement drop motion and droplet splitting. To perform ELISA, multiple fluid reservoirs for samples, enzyme-labeled antibodies, and wash buffers are present on the chip.

Example 2

Model antigen/antibody and antibody/peptide systems are used that involve the use of well-defined monoclonal, Fab and single chain fragment variable (scfv) recombinant antibody fragments or peptides to identify antibody (i.e., IgG, Fab or scfv) or peptide format that results in enhanced assay sensitivity and specificity when used in assays for serum samples. The A10B antibody binds to and captures rabbit IgG from solution. A10B monoclonal IgG, Fab or scfv antibodies are immobilized on the gold sensor surfaces using either passive adsorption, biotinylated and bound to avidin/streptavidin, or engineered (e.g., cysteine amino acid) sulfhydryl (—SH) group. A direct ELISA using rabbit IgG conjugated to peroxidase (rabbit IgG/HRP) and $H_2O_2$ is used to determine if the A10B capture antibody retains biological activity. For an indirect or sandwich-based ELISA, rabbit IgG captured by A10B is detected using commercially available goat anti-rabbit IgG conjugated to enzymes (e.g., peroxidase, alkaline phosphatase, beta-galactosidase, etc.) and a suitable chemical substrate to determine assay sensitivity and specificity.

Figure 10:
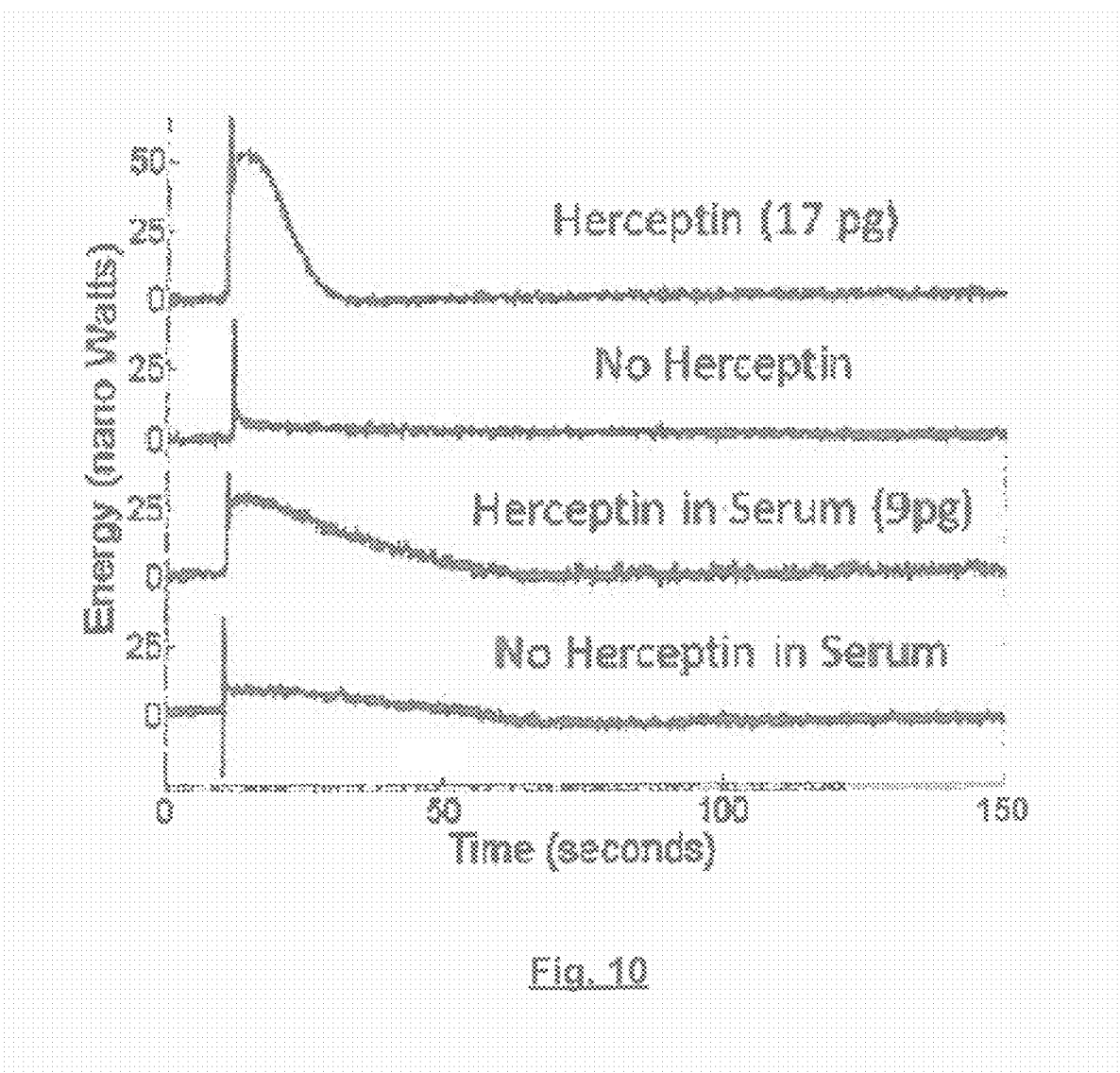
FIG. 10 is a graph showing the use of HRP for enzyme amplification to detect HERCEPTIN bound to a Her2 mimetic at therapeutic concentrations in buffer and serum using a calorimeter of the present disclosure.

A number of A10B scfv mutants have been engineered to display amino acids (e.g., cysteine) that can be used to directly couple the A10B scfv to surfaces (e.g., gold surfaces) as a self-assembled monolayer (SAM) to capture rabbit IgG out of samples. The A10B scfv and IgG monoclonal antibodies have also been used in assays involving SPR and/or mass spectrometry. The CH-19 synthetic peptide is a HER2 mimetic to which HERCEPTIN binds. Our preliminary data were obtained utilizing biotinylated CH-19 peptide immobilized onto an avidin-coated gold sensor surface and an HRP-conjugated anti-human IgG as a secondary capture reagent. Subsequently, $H_2O_2$ was used to detect HERCEPTIN spiked into buffer and pooled human normal serum samples using nanocalorimetry FIG. 10. We have already procured well-annotated and de-identified normal and breast cancer patient serum/plasma samples from commercial sources. The CH-19 peptide is used to detect and quantify HERCEPTIN in HERCEPTIN-treated breast cancer patient samples.

Sample/Serum Treatment

Serum matrix effects are components of serum (e.g., anti-antibodies) that can bind to and interfere with reagents (e.g., synthetic peptides) used in immunoassays to detect analytes (e.g., HERCEPTIN). Heat is used to treat and disrupt/denature components in human serum (i.e., serum matrix effects such as those involving anti-antibodies) that can interfere with antigen/antibody interactions. The 2B4 scfv is a high affinity scfv that can be used to specifically capture heat-denatured HERCEPTIN from solution. Serum samples or a negative control (e.g., Bevacizumab/Avastin) is briefly heated from 65-90° C. for several seconds then passed over a sensor surface of the device bearing avidin/streptavidin to which biotinylated 2B4 scfv or a negative control scfv (e.g., A10B scfv) have been immobilized. Bound HERCEPTIN is detected using commercially available peroxidase conjugated anti-human IgG and $H_2O_2$.

Enzyme Amplification

The above data demonstrate that we can detect the heat generated by HRP using $H_2O_2$ as an enzyme substrate within seconds in nanoliter droplets. Horseradish-peroxidase is very often linked to secondary antibodies in conventional colorimetric ELISAs. However, other enzyme systems are available and tested for suitability in the calorimeter of the present disclosure. Catalase, for example, has one of the highest turnover numbers of all the enzymes converting peroxide. A comparison of the thermal response between horseradish peroxidase and catalase demonstrating picogram sensitivities is shown in FIG. 9. Other enzyme and substrates can include: alkaline phosphatase with p-nitrophenyl phosphate as the chemical substrate; beta-galactosidase with 4-methylumbelliferone β-D-galactopyranoside as the substrate; and urease with urea as the substrate. All enzymes can be coupled to antibodies using commercially available crosslinking agents. For each of the enzyme and substrate systems, optimal enzyme:antibody conjugation ratios, substrate concentrations and the limit of detection for each enzyme when coupled to the same antigen-specific antibody and used in the calorimeter of the present disclosure to detect the same antigen are determined.

Determination of Calorimeter Assay Sensitivity

Samples (e.g., human serum samples containing an antigen or analyte such as the HERCEPTIN therapeutic McAb) are introduced into the calorimeter via a capillary port. Digital microfluidics is used to transport samples from the port to a staging site (e.g., a site containing an immobilized anti-HERCEPTIN capture antibody) and reagents (e.g., wash buffers, enzyme conjugated antibodies and chemical substrates) to carry out the ELISA reactions. Heat is generated from the antibody-conjugated enzyme/substrate reaction at the staging site to produce an electronic signal—the magnitude and temporal profile of the signal is indicative of antigen (e.g., HERCEPTIN) presence and can be directly converted into a concentration (FIG. 9). The detection as well as the capture step can be repeated multiple times in order to increase the calorimeter sensitivity by bringing new enzyme substrate and sample to the central reaction zone. Digital microfluidics can also be used to transport serum/plasma samples to a pre-processing area where samples can be briefly heated (under controlled conditions to avoid evaporation) to disrupt serum matrix effects (e.g., anti-antibodies) to further enhance assay specificity and sensitivity.

The present invention is a method of detecting a target analyte in a fluid sample, using an analysis device including a supporting structure configured to receive an insert having a calorimeter and a surface which is capable of being functionalized with a specified bound analyte: binding a sample to the specified bound analyte; applying a secondary capture agent including an enzyme to the functionalized surface; allowing the secondary capture agent to bind to the specified bound analyte; removing any unbound secondary capture agent from the functionalized surface; applying a substrate configured to react with at least one of the secondary capture agent and the sample generating a thermal change; and measuring a generated thermal change over a specified time period.

The method further includes wherein the step of applying a substrate further includes the step of selecting a substrate specifically configured to react with the enzyme of the secondary capture agent and generate a thermal change.

The method further includes wherein the insert includes a central reaction zone configured to receive a sample volume of a specified size and wherein the step of binding a sample further includes a step of applying multiple droplets of sample, each having a volume less than the specified size.

The method further includes a step of removing any unbound sample from the functionalized surface before the step of applying a secondary capture agent.

The method includes wherein the insert includes a plurality of reaction zones and wherein the method further includes the step of performing the steps in parallel in at least two of the plurality of reaction zones.

The method further includes a step of providing the insert including a thermally conductive surface layer having at least one calorimeter formed from at least one of a thermopile and tracks of two dissimilar metals deposited on the membrane.

The method further includes a step of functionalizing the surface with a specified bound analyte.

The method further includes a step of providing a surface functionalized with a specified bound analyte.

The method further includes a step of hermetically sealing the sample, secondary capture agent and substrate before said step of measuring the generated thermal change.

The method further includes the steps of measuring the mass applied to the functionalized surface during each of the steps of binding a sample, applying a secondary capture agent, and applying a substrate.

The method further includes measuring the mass using at least one of a strain gauge, quartz crystal microbalance, an optical measuring device or any other mechanism for measuring an applied mass in nanoliter or picoliter volumes.

The method wherein the step of measuring the generated thermal change is performed without hermetically sealing the sample, secondary capture agent and substrate.

The method wherein the step of measuring the generated thermal change further includes a step of adjusting the measured thermal change to account for evaporation of at least one of the sample, secondary capture agent and substrate.

The method wherein the step of binding a sample includes a step of measuring a sample volume of less than 100 nanoliters for binding to the specified bound analyte and the step of applying a secondary capture agent includes a step of measuring a sample volume of less than 100 nanoliters for applying.

The method wherein the step of binding a sample includes a step of measuring a sample volume of less than 100 nanoliters.

The method wherein the insert includes at least one reaction zone, and the time constant tau given by the ratio of the total thermal mass to the total thermal conductivity of the calorimeter is set to less than 1 second.

The method wherein the step of binding the secondary capture agent to the sample includes a step of bringing multiple secondary capture agent droplets into contact with the specified bound analyte.

In another embodiment the invention comprises a method of detecting a target analyte in a fluid sample, using an analysis device including a supporting structure configured to receive an insert having a calorimeter and a surface which is capable of being functionalized with a specified bound analyte: measuring a sample volume of less than 100 nL; binding a sample to the specified bound analyte; applying a secondary capture agent including an enzyme to the functionalized surface; allowing the secondary capture agent to bind to the sample; removing any unbound secondary capture agent from the functionalized surface; applying a substrate configured to react with at least one of the secondary capture agent and the sample generating a thermal change; and measuring the generated thermal change over a specified time period.

The method wherein said step of applying a secondary capture agent includes a step of measuring a volume of secondary capture agent of less 100 nanoliters.

The method wherein said step of applying a substrate includes a step of measuring a volume of the substrate step of less 100 nanoliters.

The method further including the steps of: applying a sample volume measured during said step of measuring a sample volume to the surface, between said steps of measuring a sample volume and binding a sample; determining the amount of secondary capture agent to be applied during said step of applying a secondary capture agent, based upon an amount of sample volume successfully applied to the surface during said step of applying to the surface a sample volume; determining the amount of substrate based upon at least one of the amount of sample volume successfully applied to the surface during said step of applying to the surface sample volume and the amount of secondary capture agent successfully applied during said step of applying a secondary capture agent.

The method wherein said insert includes a central reaction zone configured to receive a sample volume of a specified size and wherein said step of binding a sample further includes the step of: applying multiple droplets of sample, each having a volume less than the specified size; and removing any unbound sample from the functionalized surface before said step of applying a secondary capture agent.

The method further including a step of functionalizing the surface with a specified bound analyte.

The method further including a step of providing a surface functionalized with a specified bound analyte.

The method further including a step of hermetically sealing the sample, secondary capture agent and substrate before said step of measuring the generated thermal change.

The method further including the steps of measuring the mass applied to the functionalized surface during each of the steps of binding a sample, applying a secondary capture agent, and applying a substrate.

The method wherein said steps are performed without hermetically sealing the sample, secondary capture agent and substrate, while measuring the generated thermal change.

The method wherein said step of measuring the generated thermal change further includes the step of adjusting the measured thermal change to account for evaporation of at least one of the sample, secondary capture agent and substrate.

The method wherein said step of binding a sample includes a step of measuring a sample volume of less than 100 nanoliters.

The method wherein the insert includes at least one reaction zone, and the time constant tau given by the ratio of the total thermal mass to the total thermal conductivity of the calorimeter is set to less than 1 second.

The method wherein said step of measuring the generated thermal change further includes measuring the collective thermal change generated by each enzyme molecule forming the enzyme turning over multiple substrate molecules.

The method further including the step of outputting a determination of the existence or absence of the target analyte in the sample.

The method wherein said step of outputting a determination further includes the step of: storing a predicted thermal change for the presence of target analyte in the sample; comparing the generated thermal change determined in the step of measuring a generated thermal change over a specified time with the predicted thermal change stored in analysis device.

The method further including the step of: functionalizing the surface with a specified bound analyte; and encoding information on the insert including information regarding the specified bound analyte and the device is configured to receive such encoded information.

The method further including the steps of: inserting the insert into the analysis device; and automatically determining in the analysis device the specified bound analyte.

The method further including the steps of: presenting to the user a list of target analytes capable of being bound to the specified bound analyte on the insert, as determined during said step of automatically determining; and receiving an input of the desired target analyte for which the sample will be tested.

The method further including the steps of: presenting to the user a list of secondary capture agents including an enzyme that are capable of being bound to the sample during said step of allowing the secondary capture agent to bind to the sample; and receiving an input of the desired secondary capture agent.

The method further including the steps of: presenting to the user a list of substrates that are capable of generating a thermal change when reacting with the secondary capture agent including an enzyme; and receiving an input of the desired substrate.

The method further including the steps of: loading a stored predicted thermal change based at least one of: (1) the determined specified bound analyte, (2) the target analyte in the sample received during said step of receiving an input of the target analyte, (3) the desired secondary capture agent received during said step of receiving an input of the desired secondary capture agent, and (4) the desired substrate received during said step of receiving an input of the desired substrate.

The method further including the steps of: loading a stored predicted thermal change for the presence of target analyte in the sample; and comparing the generated thermal change determined in the step of measuring the generated thermal change over a specified time with the predicted thermal change stored in analysis device.

The method wherein said step of applying a secondary capture agent includes the step of bringing multiple droplets of secondary capture agent into contact with the sample.

The method further including the step of repeating the steps of applying a substrate and measuring the generated thermal change and using signal averaging to increase the signal to noise ratio when performing a step of determining the existence or absence of the target analyte in the sample.

The method wherein said step of repeating does not include any steps of adding additional sample or applying additional secondary capture agent.

The method wherein said secondary capture agent is stored in the device and said steps of applying a secondary capture agent and removing any unbound secondary capture agent are performed by the device in response receiving a sample.

The method wherein said step of measuring a sample volume is automatically performed by the device in response receiving a sample and receiving an input to start the method.

The method wherein said step of measuring a sample volume is automatically performed by the device in response to receiving a sample.

The method further including the step of providing the insert having calorimeters capable of detecting less than 10 nanoJoules of thermal change.

The method further include the step of applying a specified amount of heat before said step of measuring the generated thermal change.

The method further including the step of cooling at least the central reaction zone before said step of measuring the generated thermal change.

The method wherein the insert includes a central reaction zone having a reaction zone and a control zone and wherein said steps further include the step of adjusting the temperature of at least the reaction zone.

The method wherein the step of adjusting the temperature of the reaction zone, includes determining a desired temperature of the reaction zone to reduce thermal events relating to bindings between items which are not the target analyte and one of the sample, secondary capture agent including enzyme and substrate.

The method wherein said step of adjusting the temperature of the reaction zone further includes the steps of adjusting the temperature of the reaction zone before applying the substrate and maintaining the temperature until said step of adding the substrate.

The method wherein said surface includes a specified bound analyte configured to have affinity for the target analyte and wherein during a step of applying the sample, the specified bound analyte immobilizes said target analyte on said surface.

The method wherein the insert includes a central reaction zone and said steps further include the step of adjusting the temperature of the central reaction zone to denature the sample.

The method further including adjusting the temperature of the reaction zone before applying the substrate and maintaining the temperature until said step of adding the substrate.

The method wherein the insert includes a central reaction zone and said steps further include the step of heating the central reaction zone to break down compounds in the sample into the desired target analytes.

The method wherein said step of heating the central reaction zone includes the step of repeatable cycling the temperature of the sample above a specified temperature.

The method wherein said step of repeatable cycling the temperature above a specified temperature further includes a step of cooling between each cycling of the temperature above a specified temperature.

The method wherein said step of heating the reaction zone includes the step of thermal cycling to generate a polymerase chain reaction.

The method further including the step of measuring the temperature of the sample with the calorimeter and detection the onset of the polymerase chain reaction.

The method wherein the target analyte is a bacteria and the substrate is an antibody, and wherein said step of measuring a thermal change includes the step of measuring the interaction between the antibody and the bacteria.

The method further including the step of measuring the interactions between the bacteria and different antibodies to determine which antibody has the greatest interaction with the bacteria.

The method further including the step of obtaining a human fluid for use as a sample.

The method further including the step of striping out compounds from the sample which are not the target analyte and which are capable of binding with the secondary capture agent to create a false positive.

In another embodiment a method of detecting a target analyte in a fluid sample, using an analysis device comprising the steps of: providing an insert having a calorimeter and a surface which is functionalized with a specified bound analyte: receiving a sample; measuring a sample volume of less than 100 nL; applying the measured sample volume, from said step of measuring, to the specified bound analyte; measuring the generated thermal change over a specified time period from a reaction between the target analyte in the sample and the specified bound analyte; and determining the presence or absence of the target analyte in the sample.

The method wherein the target analyte is a pathogen and the substrate is at least one of an antibody and an antiviral, and wherein said step of measuring a thermal change includes the step of measuring the interaction between the substrate and the bacteria.

The method further including the step of measuring the interactions between the pathogen and different substrates to determine which substrate has the greatest interaction with the bacteria.

The method wherein said step of measuring interactions further includes the step of measuring changes in the metabolism of the pathogen.

The method further including the step of obtaining at least one of a human fluid and human tissue for use as a sample.

The method wherein the target analyte is cancer cells and the substrate is a chemotherapy drug, and wherein said step of measuring a thermal change includes the step of measuring the interaction between the substrate and the target analyte.

The method wherein said step of measuring the interaction between the substrate and the target analyte includes a step of measuring changes in the metabolism of the cancer cell In another embodiment a method of detecting a target analyte in a fluid sample, using an analysis device including a supporting structure configured to receive an insert having a calorimeter and a surface having a reaction zone and a control zone: applying the sample to at least the reaction zone; applying a substrate to the reaction zone and the control zone; measuring the generated thermal difference over a specified time period between the reaction zone and the control zone; continue applying the substrate to the reaction zone and the control zone during said step of measuring the generated thermal difference until the temperature difference between the reaction zone and the control zone is less than a specified differential; and generating an output related to the presence or absence of the target analyte in the sample.

In another embodiment a method of detecting a target analyte in a fluid sample, using an analysis device including a supporting structure configured to receive an insert having a calorimeter and a surface having a reaction zone and a control zone; applying the sample to at least the reaction zone; measuring the generated thermal difference over a specified time period between the reaction zone and the control zone; and generating an output related to the presence or absence of the target analyte in the sample.

The method further including the step of functionalizing the surface of the reaction zone before said step of applying the sample.

The method wherein said step of functionalizing the surface of the reaction zone specifically avoids functionalizing the surface of the control zone.

The method wherein said step of functionalizing the surface of the reaction zone includes a step of applying a specified bound analyte to the reaction zone and removing any analyte not bound to the surface of the reaction zone.

The method wherein said step of measuring the generated thermal difference over a specified time period includes the step of measuring the generated thermal difference between the control zone and the reaction zone while a reaction between the sample and the functionalized surface occurs on the reaction zone.

The method further including the step of applying a secondary capture agent including an enzyme to the surface of the reaction zone, including the specified bound analyte and the sample, and wherein said step of measuring the generated thermal difference over a specified time period includes the step of measuring the generated thermal difference between the control zone and the reaction zone while a reaction between the secondary capture agent, including an enzyme and the target analyte in the sample occurs in the reaction zone.

The method further including the step of applying a substrate to the surface of the reaction zone, including the specified bound analyte, sample and secondary capture agent and wherein said step of measuring the generated thermal difference over a specified time period includes the step of measuring the generated thermal difference between the control zone and the reaction zone while a reaction between the enzyme and the substrate occurs in the reaction zone.

The method further including the step of providing a functionalized surface wherein the reaction zone includes a specified bound analyte and said control zone does not include the specified bound analyte.

The method further including the steps of: applying a secondary capture agent including an enzyme to at least the reaction zone; removing any unbound secondary capture agent from at least the reaction zone; applying a substrate configured to react with the enzyme to generate a thermal change, and wherein said step of measuring the generated thermal difference includes the step of measuring the thermal difference while said reaction between the enzyme and substrate occurs.

The method further including the step of continuing to apply substrate while measuring the generated thermal difference.

The method wherein said step of applying a sample and a secondary capture agent each results in a specified volume applied to the surface, and wherein the volume of substrate applied during said step of applying substrate is greater than the specified volume of the sample and secondary capture agent applied.

The method further including the step of providing an insert having at least one thermopile and wherein each thermopile is operationally coupled to the reaction zone and the control zone.

The method wherein said insert includes multiple thermopiles.

In another embodiment a device for detecting a target analyte comprising: a supporting structure; a sample measuring apparatus supported by the supporting structure and including: a surface including a thermally conductive layer having reaction zone and a control zone; a thermopile operationally coupled to said reaction zone and said control zone on said thermally conductive layer; and a thermally insulated layer configured to insulate at least the reaction zone.

The method further including at least one channel configured to move at least one of sample, secondary capture agent, and substrate to the reaction zone.

From the above description of the invention, those skilled in the art will perceive improvements, changes, and modifications. For example, it will be appreciated that components of the calorimeter (e.g., the temperature sensor and the digital microfluidics) can be fabricated on the same surface of the support structure to eliminate flip chip assembly, cross plane electrical connections, and enhance sample visualization lead to a reduction of fabrication costs and increased yield. Such improvements, changes, and modifications are within the skill of the art and are intended to be covered by the appended claims. All patents, patent applications, and publication cited herein are incorporated by reference in their entirety.

We claim:
1. A method of detecting a target analyte in a fluid sample, using an analysis device including a supporting structure configured to receive an insert having a calorimeter and a surface which is capable of being functionalized with a specified bound analyte:
   binding a sample to the specified bound analyte;
   applying a secondary capture agent including an enzyme to the functionalized surface;
   allowing the secondary capture agent to bind to the specified bound analyte;
   removing any unbound secondary capture agent from the functionalized surface;
   applying a substrate configured to react with at least one of the secondary capture agent and the sample generating a thermal change;

measuring the mass applied to the functionalized surface after each of the steps of binding a sample, applying a secondary capture agent and applying a substrate and measuring a generated thermal change over a specified time period without hermetically sealing the sample, secondary capture agent and substrate.

2. The method of claim 1 wherein said step of applying a substrate further includes the step of selecting a substrate specifically configured to react with the enzyme of the secondary capture agent and generate a thermal change.

3. The method of claim 1 wherein said insert includes a central reaction zone configured to receive a sample volume of a specified size and wherein said step of binding a sample further includes a step of applying multiple droplets of sample, each having a volume less than the specified size.

4. The method of claim 1 further including a step of removing any unbound sample from the functionalized surface before said step of applying a secondary capture agent.

5. The method of claim 1 wherein the insert includes a plurality of reaction zones and wherein the method further includes the step of performing the steps of claim 1 in parallel in at least two of said plurality of reaction zones.

6. The method of claim 1 further including a step of providing the insert including a thermally conductive surface layer having at least one calorimeter formed from at least one of a thermopile and tracks of two dissimilar metals deposited on the membrane.

7. The method of claim 1 further including a step of functionalizing the surface with a specified bound analyte.

8. The method of claim 1 further including a step of providing a surface functionalized with a specified bound analyte.

9. The method of claim 1 wherein said step of measuring the generated thermal change further includes a step of adjusting the measured thermal change to account for evaporation of at least one of the sample, secondary capture agent and substrate.

10. The method of claim 1 wherein said step of binding a sample includes a step of measuring a sample volume of less than 100 nanoliters for binding to the specified bound analyte and said step of applying a secondary capture agent includes a step of measuring a sample volume of less than 100 nanoliters for applying.

11. The method of claim 1 wherein said step of binding a sample includes a step of measuring a sample volume of less than 100 nanoliters.

12. The method of claim 1 wherein the insert includes at least one reaction zone, and the time constant tau given by the ratio of the total thermal mass to the total thermal conductivity of the calorimeter is set to less than 1 second.

13. The method of claim 1 wherein said step of binding the secondary capture agent to the sample includes a step of bringing multiple secondary capture agent droplets into contact with the specified bound analyte.

14. The method of claim 1 wherein said method further comprises a step of measuring a sample volume of less than 100 nL.

15. A method of detecting a target analyte in a fluid sample, using an analysis device including a supporting structure configured to receive an insert having a calorimeter and a surface which is capable of being functionalized with a specified bound analyte:
measuring a sample volume of less than 100 nL;
binding a sample to the specified bound analyte;
applying a secondary capture agent including an enzyme to the functionalized surface;
allowing the secondary capture agent to bind to the sample;
removing any unbound secondary capture agent from the functionalized surface;
applying a substrate configured to react with at least one of the secondary capture agent and the sample generating a thermal change;
measuring the mass applied to the functionalized surface during each of the steps of binding a sample, applying a secondary capture agent, and applying a substrate; and
measuring the generated thermal change over a specified time period, wherein said steps are performed without hermetically sealing the sample, secondary capture agent and substrate, while measuring the generated thermal change.

16. The method of claim 15 wherein said step of applying a secondary capture agent includes a step of measuring a volume of secondary capture agent of less 100 nanoliters.

17. The method of claim 15 wherein said step of applying a substrate includes a step of measuring a volume of the substrate step of less 100 nanoliters.

18. The method of claim 15 further including the steps of:
applying a sample volume measured during said step of measuring a sample volume to the surface, between said steps of measuring a sample volume and binding a sample;
determining the amount of secondary capture agent to be applied during said step of applying a secondary capture agent, based upon an amount of sample volume successfully applied to the surface during said step of applying to the surface a sample volume; and
determining the amount of substrate based upon at least one of the amount of sample volume successfully applied to the surface during said step of applying to the surface sample volume and the amount of secondary capture agent successfully applied during said step of applying a secondary capture agent.

19. The method of claim 15 wherein said insert includes a central reaction zone configured to receive a sample volume of a specified size and wherein said step of binding a sample further includes the step of:
applying multiple droplets of sample, each having a volume less than the specified size; and
removing any unbound sample from the functionalized surface before said step of applying a secondary capture agent.

20. The method of claim 15 further including a step of functionalizing the surface with a specified bound analyte.

21. The method of claim 15 further including a step of providing a surface functionalized with a specified bound analyte.

22. The method of claim 15 wherein said step of measuring the generated thermal change further includes the step of adjusting the measured thermal change to account for evaporation of at least one of the sample, secondary capture agent and substrate.

23. The method of claim 15 wherein said step of binding a sample includes a step of measuring a sample volume of less than 100 nanoliters.

24. The method of claim 15 wherein the insert includes at least one reaction zone, and the time constant tau given by the ratio of the total thermal mass to the total thermal conductivity of the calorimeter is set to less than 1 second.

25. The method of claim 15 wherein said step of measuring the generated thermal change further includes measuring the collective thermal change generated by each enzyme molecule forming the enzyme turning over multiple substrate molecules.

26. The method claim 15 further including the step of outputting a determination of the existence or absence of the target analyte in the sample.

27. The method of claim 26 wherein said step of outputting a determination further includes the step of:
storing a predicted thermal change for the presence of target analyte in the sample;
comparing the generated thermal change determined in the step of measuring a generated thermal change over a specified time with the predicted thermal change stored in analysis device.

28. The method of claim 15 further including the step of:
functionalizing the surface with a specified bound analyte; and
encoding information on the insert including information regarding the specified bound analyte and the device is configured to receive such encoded information.

29. The method of claim 28 further including the steps of:
inserting the insert into the analysis device; and
automatically determining in the analysis device the specified bound analyte.

30. The method of claim 29 further including the steps of:
presenting to the user a list of target analytes capable of being bound to the specified bound analyte on the insert, as determined during said step of automatically determining; and
receiving an input of the desired target analyte for which the sample will be tested.

31. The method of claim 30 further including the steps of:
presenting to the user a list of secondary capture agents including an enzyme that are capable of being bound to the sample during said step of allowing the secondary capture agent to bind to the sample; and
receiving an input of the desired secondary capture agent.

32. The method of claim 31 further including the steps of:
presenting to the user a list of substrates that are capable of generating a thermal change when reacting with the secondary capture agent including an enzyme; and
receiving an input of the desired substrate.

33. The method of claim 32 further including the steps of:
loading a stored predicted thermal change based at least one of: (1) the determined specified bound analyte, (2) the target analyte in the sample received during said step of receiving an input of the target analyte, (3) the desired secondary capture agent received during said step of receiving an input of the desired secondary capture agent, and (4) the desired substrate received during said step of receiving an input of the desired substrate.

34. The method of claim 15 further including the steps of:
loading a stored predicted thermal change for the presence of target analyte in the sample; and
comparing the generated thermal change determined in the step of measuring the generated thermal change over a specified time with the predicted thermal change stored in analysis device.

35. The method of claim 15 wherein said step of applying a secondary capture agent includes the step of bringing multiple droplets of secondary capture agent into contact with the sample.

36. The method of claim 15 further including the step of repeating the steps of applying a substrate and measuring the generated thermal change and using signal averaging to increase the signal to noise ratio when performing a step of determining the existence or absence of the target analyte in the sample.

37. The method of claim 36 wherein said step of repeating does not include any steps of adding additional sample or applying additional secondary capture agent.

38. The method of claim 15 wherein said secondary capture agent is stored in the device and said steps of applying a secondary capture agent and removing any unbound secondary capture agent are performed by the device in response receiving a sample.

39. The method of claim 15 wherein said step of measuring a sample volume is automatically performed by the device in response receiving a sample and receiving an input to start the method.

40. The method of claim 15 wherein said step of measuring a sample volume is automatically performed by the device in response to receiving a sample.

41. The method of claim 15 further including the step of providing the insert having calorimeters capable of detecting less than 10 nanoJoules of thermal change.

42. The method of claim 15 further include the step of applying a specified amount of heat before said step of measuring the generated thermal change.

43. The method of claim 15 further including the step of cooling at least the central reaction zone before said step of measuring the generated thermal change.

44. The method of claim 15 wherein the insert includes a central reaction zone having a reaction zone and a control zone and wherein said steps further include the step of adjusting the temperature of at least the reaction zone.

45. The method of claim 44 wherein the step of adjusting the temperature of the reaction zone, includes determining a desired temperature of the reaction zone to reduce thermal events relating to bindings between items which are not the target analyte and one of the sample, secondary capture agent including enzyme and substrate.

46. The method of claim 44 wherein said step of adjusting the temperature of the reaction zone further includes the steps of adjusting the temperature of the reaction zone before applying the substrate and maintaining the temperature until said step of adding the substrate.

47. The method of claim 15 wherein said surface includes a specified bound analyte configured to have affinity for the target analyte and wherein during a step of applying the sample, the specified bound analyte immobilizes said target analyte on said surface.

48. The method of claim 15 wherein the insert includes a central reaction zone and said steps further include the step of adjusting the temperature of the central reaction zone to denature the sample.

49. The method of claim 48 further including adjusting the temperature of the reaction zone before applying the substrate and maintaining the temperature until said step of adding the substrate.

50. The method of claim 15 wherein the insert includes a central reaction zone and said steps further include the step of heating the central reaction zone to break down compounds in the sample into the desired target analytes.

51. The method of claim 50 wherein said step of heating the central reaction zone includes the step of repeatable cycling the temperature of the sample above a specified temperature.

52. The method of claim 51 wherein said step of repeatable cycling the temperature above a specified temperature further includes a step of cooling between each cycling of the temperature above a specified temperature.

53. The method of claim 52 wherein said step of heating the reaction zone includes the step of thermal cycling to generate a polymerase chain reaction.

54. The method of claim 52 further including the step of measuring the temperature of the sample with the calorimeter and detection the onset of the polymerase chain reaction.

55. The method of claim 15 wherein the target analyte is a bacteria and the substrate is an antibody, and wherein said step of measuring a thermal change includes the step of measuring the interaction between the antibody and the bacteria.

56. The method of claim 55 further including the step of measuring the interactions between the bacteria and different antibodies to determine which antibody has the greatest interaction with the bacteria.

57. The method of claim 56 further including the step of obtaining a human fluid for use as a sample.

58. The method of claim 15 further including the step of striping out compounds from the sample which are not the target analyte and which are capable of binding with the secondary capture agent to create a false positive.

\* \* \* \* \*